United States Patent [19]
Takeuchi et al.

[11] Patent Number: 5,831,072
[45] Date of Patent: Nov. 3, 1998

[54] PROCESS FOR THE PREPARATION OF 2'-DEOXY-2'-HALOCOFORMYCINS OR STEROISOMERS THEREOF

[75] Inventors: Tomio Takeuchi; Sumio Umezawa; Tsutomu Tsuchiya; Yoshiaki Takahashi, all of Tokyo, Japan

[73] Assignee: Zaidan Hojin Biseibutsu Kagaku Kenkyu Kai, Tokyo, Japan

[21] Appl. No.: 808,033

[22] Filed: Mar. 4, 1997

[30] Foreign Application Priority Data

Mar. 7, 1996 [JP] Japan ................................. 8-078084

[51] Int. Cl.$^6$ .................................................. C07H 19/23
[52] U.S. Cl. ..................................... 536/27.11; 536/27.12; 536/27.6; 536/27.8; 536/28.8; 514/45; 514/46
[58] Field of Search ........................... 536/27.11, 27.13, 536/27.6, 28.8; 514/45, 46

[56] References Cited

U.S. PATENT DOCUMENTS

| | | | |
|---|---|---|---|
| 3,923,785 | 12/1975 | Ryder et al. | 536/27.13 |
| 4,117,229 | 9/1978 | Baker et al. | 536/27.11 |
| 4,713,372 | 12/1987 | Schaumber et al. | 514/45 |

FOREIGN PATENT DOCUMENTS

| | | |
|---|---|---|
| 61-199797 | 9/1986 | Japan . |
| 63-275596 | 1/1988 | Japan . |
| 9010137 | 5/1993 | WIPO . |

OTHER PUBLICATIONS

Isshiki et al., "Synthesis of Azepinomycin and β-D-ribofuranoside," *J. Antibiotics*, 40(10), 1461–1463 (1987); *Chem. Abstr.*, 109(5), p. 652, Abstr. No. 38163n (Aug. 1, 1988); only abstract provided.

Omura et al., "Adechlorin, A New Adenosine Deaminase Inhibitor Containing Chlorine. Production, Isolation and Properties," *J. Antibiotics*, 38(8), 1008–1015 (1985); *Chem. Abstr.*, 103(19), p. 380, Abstr. No. 156967b (Nov. 11, 1985); only abstract provided.

Schaumberg et al., "2'-Chloropentostatin, A New Inhibitor of Adenosine Aminase," *J. Organic Chem.*, 50(10), 1651–1656 (May 17, 1985).

Suhadolnik et al., "Stereospecific 2'-Amination and 2'Chlorination of Adenosine by *Actinomadura* in the Biosynthesis of 2'–Amino–2'–dexyadenosine and 2'–Chloro–2'–deoxycoformycin," *Arch. Biochem. Biophys.*, 270(1), 347–382 (Apr. 1989).

Woo et al., "Synthesis of [5–$^{14}$C] Pentostatin, An Antileukemic Agent and Potent Adenosine Deaminase Inhibitor," *J. Labelled Compounds Radiopharmaceuticals*, 28(4), 445–454 (Apr. 1990).

*Primary Examiner*—John Kight
*Assistant Examiner*—L. Eric Crane
*Attorney, Agent, or Firm*—Larson & Taylor

[57] ABSTRACT

An object of this invention is to provide a novel process for the synthesis of a 2'-deoxy-2'-halocoformycin having an inhibitory activity against adenosine deaminase in a practically high yield. Thus, there is provided a process comprising multi-stage reactions with using as the starting intermediate a tert-butyl 1-(3,5-di-O-acyl-2-deoxy-2-halo-β-D-ribofuranosyl or arabinofuranosyl)-5-aminoimidazole-4-carboxylate of formula (II)

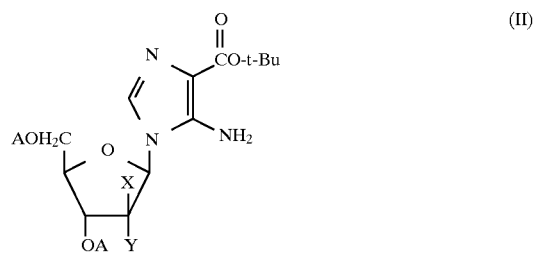

whereby there are produced a 2'-deoxy-2'-halocoformycin or a 2'-deoxy-2'-epi-2'-halocoformycin of formula (I-a)

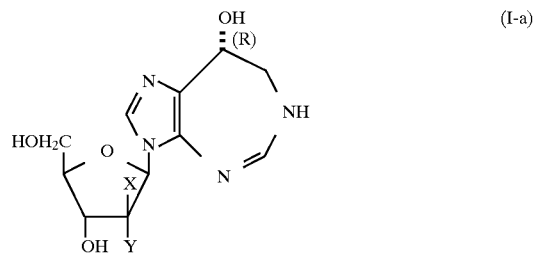

and also a 2'-deoxy-8-epi-2'-halocoformycin or a 2'-deoxy-8,2'-diepi-2'-halocoformycin of formula (I-b)

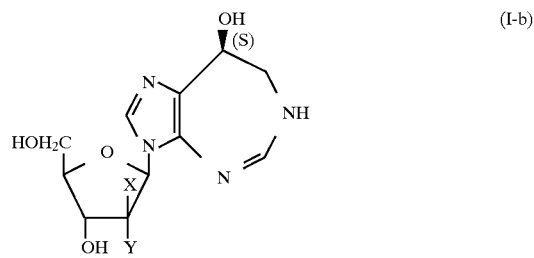

It is expectable that a 2'-deoxy-2'-halocoformycin and epimers thereof are useful as a drug for lymphocytic leukemias and as drugs for various diseases attributable to the actions of adenosine deaminase.

5 Claims, No Drawings

PROCESS FOR THE PREPARATION OF 2'-DEOXY-2'-HALOCOFORMYCINS OR STEROISOMERS THEREOF

TECHNICAL FIELD OF THE INVENTION

This invention relates to a process for the preparation of 2'-deoxy-2'-fluorocoformycin or other 2'-deoxy-2'-halocoformycins and their several stereoisomers which possess a high inhibitory activity against adenosine deaminase and an antitumor activity useful for the therapeutic treatments of lymphocytic leukemias and lymphomas. This invention further relates to novel intermediate compounds to be used for the preparation of 2'-deoxy-2'-halocoformycins, namely a tert-butyl 1-(3,5-di-O-acyl-2-deoxy-2-halo-β-D-ribofuranosyl or arabinofuranosyl)-5-aminoimidazole-4-carboxylate and a tert-butyl 1-(3,5-di-O-acyl-2-deoxy-2-halo-β-D-ribofuranosyl or arabinofuranosyl)-5-phthalimidoimidazole-4-carboxylate.

BACKGROUND OF THE INVENTION

Coformycin is known as an antibiotic of nucleoside type having an enzyme-inhibitory activity against an enzyme, adenosine deaminase (see, for example, Japanese patent Publication Sho-45-12278 and the "Journal of Antibiotics", A 20, p.227, 1967). However, coformycin is defective in that it is unstable in aqueous solutions under an acidic condition (refer to Japanese Patent Publication Sho-60-992 and U.S. Pat. No. 4,151,374). Also its known homologues are 2'-deoxycoformycin (another name: pentostatin) and 2'-chloropentostatin (see, for example, U.S. Pat. No. 4,713,372 and the "Journal of Antibiotics", Vol. XXXVIII, No. 10, pp.1344–1349, October, 1985).

These coformycin homologues are known to have an inhibitory activity against adenosine deaminase, and owing to this, they exhibit an antitumor activity, or possess such biological activity that they can maintain or increase the antitumor or antiviral activity of some other antitumor or antiviral agents when they are used in combination therewith [refer, for example, to a paper of Spiers et al., "Remissions in hairy cell leukemia with pentostatin (2'-deoxycoformycin)" described in the New Engl. J. Med., 316, pp.825–830, 1987; a paper of Deanen et al., "Successful chemotherapy with deoxycoformycin in adult T-cell lymphomaleukemia" described in the Brit. J. Haematol., 58, p.723, 1984); a paper of Yamaguchi et al., "Clinical consequences of 2'-deoxycofomycin treatment in patients with refractory adult T-cell leukemia" described in the Leukemia Res., 10, pp.989–993, 1986].

In particular, 2'-deoxycoformycin (another name: pentostatin) has a strong inhibitory activity against adenosine deaminase and can act to specifically hinder such lymphocytic cells containing much adenosine deaminase and thus has been utilized as a therapeutic agent for acute lymphocytic leukemia and adult T-cell leukemia (see the "Therapeutics", 22, No. 2, pp. 71–75, 1989; and a Japanese book "Antiviral agents" written by Onodera et al., pp. 194–195, published by Gakkai-Shuppan Center on Feb. 20, 1991, First Edition).

It is also known, however, that coformycin and pentostatin are unstable in acidic aqueous solutions and exhibit a fairly high acute toxicity to mammals, so that they are often disadvantageous in their practical applications as medicines. In consequence, there still exist keen demands in the art to provide such novel coformycin derivatives which possess a strong enzyme-inhibitory activity against adenosine deaminase, are stable in acidic aqueous solutions and are of low toxicity.

Coformycin is a compound represented by the following formula (A):

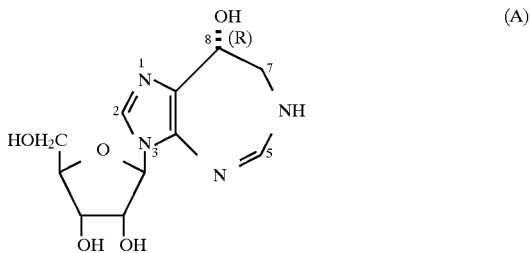

which is chemically named as (8R)-3-(β-D-ribofuranosyl)-3,6,7,8-tetrahydroimidazo[4,5-d][1,3]diazepin-8-ol. One method known for synthesizing coformycin comprises starting from 9-β-D-ribofuranosylpurine (see Japanese Patent Publication Sho-52-958 and "J. A. C. S.", 96, p. 4326, 1974).

Another method also known for the synthesis of coformycin comprises preparing and using 5-amino-1-(2,3,5-tri-O-acetyl-β-D-ribofuranosyl)imidazole-4-carboxylic acid as a starting material which is processed by multi-stage reactions to produce 3-(β-D-ribofuranosyl)-6,7-dihydroimidazo[4,5-d][1,3]diazepin-8(3H)-one as an intermediate, followed by reducing the intermediate (see H. J. Thomas et al., "Nucleosides & Nucleotides", 5, No. 4, pp. 431–439, 1986).

A process for the synthesis of 2'-deoxycoformycin, that is, pentostatin, is also known (see, for example, a paper of Chan et al., given in J. Org. Chem., 47, pp. 3457–3464, 1982). 2'-Chloro-2'-deoxycoformycin (another name: 2'-chloropentostatin) was first produced by a fermentation of one strain of actinomycetes (deposited as ATCC 39365) (see Japanese Patent Application Kokai Sho-60-209598 and European Patent Application First-Publication No. 0156524), but no method for the chemical sysnthesis of this compound has been reported yet.

Meanwhile, we, the present inventors, were making our investigations with the intention of synthesizing novel coformycin derivatives, and as a result we have already succeeded in synthesizing 3,5-di-O-benzoyl-2-deoxy-2-fluoro-α,β-D-ribofuranosyl bromide. This compound was then successfully processed through multi-stage synthetic reactions to produce 2'-deoxy-2'-fluorocoformycin represented by the following formula (B)

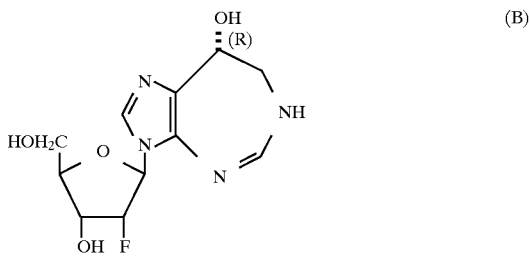

and also to produce 2'-deoxy-8-epi-2'-fluorocoformycin represented by the following formula (C)

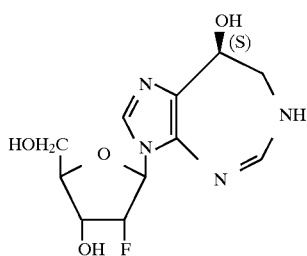

as a second product.

We have further continued our investigations with starting from a known compound, 3,5-di-O-benzoyl-2-deoxy-2-fluoro-α-D-arabinofuranosyl bromide, and through multi-stage synthetic reactions, we have succeeded in synthesizing further two compounds, i.e. 2'-deoxy-2'-epi-2'-fluorocoformycin represented by the following formula (D)

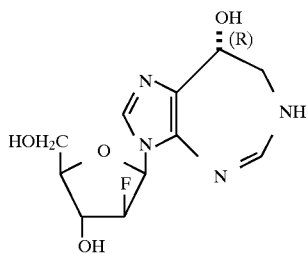

and 2'-deoxy-8,2'-diepi-2'-fluorocoformycin represented by the following formula (E)

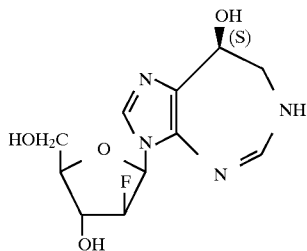

These four 2'-fluoro derivatives of coformycin represented by the above formulae (B), (C), (D) and (E) have been found to possess strong enzyme-inhibitory activities (see International Laid-Open publication WO93/10137 of PCT Application PCT/JP92/01489 and European Patent Application First-Publication No. 0643069A1 and U.S. patent application Ser. No. 08/240,777). It is believed that the compounds of the formulae (B)–(E) be useful for therapy of human acute lymphocytic leukemias on the basis of their strong inhibitory activity against adenosine deaminase.

In the above-mentioned process which we already have developed and by which 2'-deoxy-2'-fluorocoformycin of the formula (B) and 2'-deoxy-8-epi-2'-fluorocoformycin of the formula (C) could be synthesized, there was conducted, for the purpose of preparing the starting sugar, such a method for the preparation of 3,5-di-O-benzoyl-2-deoxy-2-fluoro-α,β-D-ribofuranosyl amine, which comprises providing as the starting compound methyl 3-deoxy-3-fluoro-β-D-allopyranoside (a known compound), hydrolyzing the starting compound with an aqueous hydrochloric acid to give 3-deoxy-3-fluoro-D-allopyranose, oxidizing the resulting compound with lead tetra-acetate in acetic acid at room temperature to form 2-deoxy-2-fluoro-4-O-formyl-D-ribose, deformylating the 2-deoxy-2-fluoro-4-O-formyl-D-ribose in an acidic aqueous solution under heating at 70°–90° C., thereby causing a ring-closing reaction again to produce 2-deoxy-2-fluoro-α,β-D-ribofuranose, and then carrying out further several steps to afford finally the 3,5-di-O-benzoyl-2-deoxy-2-fluoro-α,β-D-ribofuranosyl amine.

Further, in the above-mentioned process which we already successfully developed for the preparation of 2'-deoxy-2'-epi-2'-fluorocoformycin of the formula (D) and 2'-deoxy-8,2'-diepi-2'-fluorocoformycin of the formula (E), there was conducted for the purpose of preparing the starting sugar, such a method for the preparation of 3,5-di-O-benzoyl-2-deoxy-2-fluoro-α,β-D-arabinofuranosyl amine, which comprises providing as the starting compound 3,5-di-O-benzoyl-2-deoxy-2-fluoro-α-D-arabinofuranosyl bromide (a known compound) and carrying out a series of reaction steps similar to those given above to produce 3,5-di-O-benzoyl-2-deoxy-2-fluoro-α,β-D-arabinofuranosyl amine (see Synthetic Process Charts A and B of the PCT Application International Laid-Open publication WO93/10137 and European patent Application First Publication No. 0643069 A1 above-referred to).

In the above-mentioned process which we employed for the preparation of 2'-deoxy-2'-fluorocoformycin of the formula (B) and the epimers of 2'-deoxy-2'-fluorocoformycin of the formulae (C)–(E), there are further conducted such stages wherein 3,5-di-O-benzoyl-2-deoxy-2-fluoro-α,β-D-ribofuranosyl or arabinofuranosyl amine as prepared in the above and represented by the general formula (F)

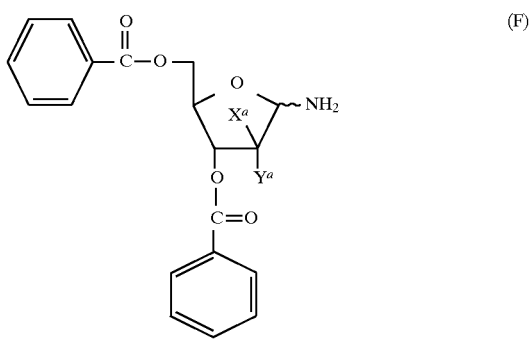

where either $X^a$ is a hydrogen atom and $Y^a$ is a fluorine atom, or $X^a$ is a fluorine atom and $Y^a$ is a hydrogen atom, was reacted with ethyl N-(α-cyano-α-ethoxycarbonylmethyl)formimidate of the following formula (G)

(which compound may be prepared in the same manner as in the method as described in a paper of D. H. Robinson et al., published on J. C. S. Perkin I, p. 1715, 1972) by heating them together under reflux according to the method of G. Mackenzie et al., as described in the "J. C. S. Chem. Comm.", pp. 453–455 (1976), thereby to yield a mixture of ethyl 5-amino-1-(3,5-di-O-benzoyl-2-deoxy-2-fluoro-β-D-ribofuranosyl or arabinofuranosyl)imidazole-4-carboxylate represented by the following formula (H)

and the α-isomer thereof represented by the following formula (H')

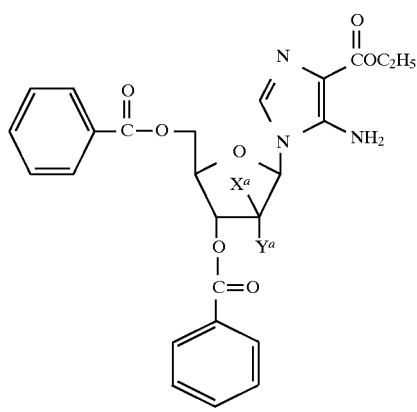

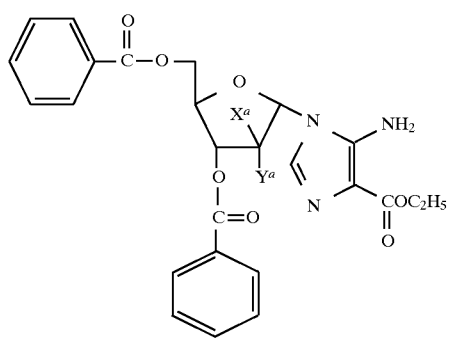

and wherein the resulting mixture was then subjected to silica gel column chromatography (as developed with a mixed solvent: ethyl acetate-chloroform), to isolate the above α-isomer and β-isomer, separately.

Then, the β-isomer of the formula (H) so isolated was further treated with sodium hydroxide in an aqueous dioxane under heating in order to remove the benzoyl group and the ester-forming ethyl group therefrom. Thus, there was obtained 5-amino-1-(2-deoxy-2-fluoro-β-D-ribofuranosyl or arabinofuranosyl)imidazole-4-carboxylic acid represented by the following formula (J)

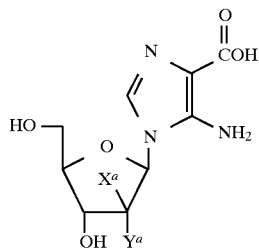

where $X^a$ and $Y^a$ are as defined above.

Subsequently, the compound of the formula (J) was reacted with acetic anhydride in pyridine at room temperature in order to protect the hydroxyl groups of the sugar moiety of said compound. Thus, there was afforded 1-(3,5-di-O-acetyl-2-deoxy-2-fluoro-β-D-ribofuranosyl or arabinofuranosyl)-5-aminomidazole-4-carboxylic acid represented by the following formula (K)

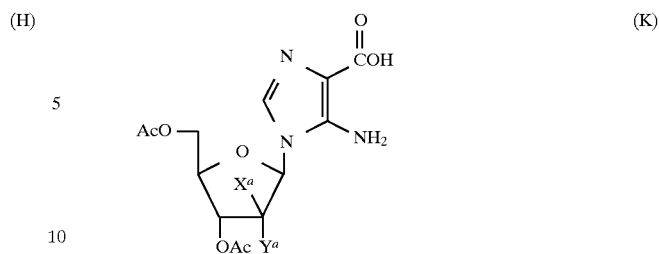

where $X^a$ and $Y^a$ have the same meanings as defined above and Ac is acetyl group (the same affreviation applies to hereinafter).

2'-Deoxy-2'-fluorocoformycin of the formula (B) and the stereoisomers thereof [namely, the compounds of formulae (C)–(E)] were synthesized with starting from the compound of the formula (K) through eight steps (see Synthetic Process Charts A and B of the PCT Application International Laid-Open publication WO93/10137 and European Patent Application First Publication No. 0643069A1 above-referred to).

As we already presented and explained above, the aforesaid process for the preparation of 2'-deoxy-2'-fluorocoformycin of the formula (B) and stereoisomers thereof through the compound of the formula (H) and the compound of the formula (J) is not satisfactorily efficient as a whole, since at a low level of about 1% was the overall yield of the desired product, including the sum of 2'-deoxy-2'-fluorocoformycin of the formula (B) and its 8-epimer [ie., compound of the formula (C)], as calculated on the basis of 3,5-di-O-benzoyl-2-deoxy-2-fluoro-α,β-D-ribofuranosyl or arabinofuranosyl amine employed. Particularly, the reaction steps which were effected with starting from the sugar amine of the formula (F) and arriving at the production of the di-O-acyl-protected 5-amino-1-(2-deoxy-2-fluoro-β-D-ribofuranosyl or arabinofuranosyl)imidazole-4-carboxylic acid of the formula (K) are required to achieve the de-esterification reaction by alkaline hydrolysis, the deprotection reaction of hydroxyl groups and the re-protection reaction of the hydroxyl groups of the sugar moiety, so that the attainable yield of the desired compound of formula (K) is low and is, in fact, at about 10% level as calculated on the basis of the sugar amine of formula (F).

Moreover, the aforesaid process already presented by us has such disadvantage that, among the nearly ten reaction steps as required to produce the compound of formula (B) and the compound of formula (C) by derivation of the compound of formula (K), about five reaction steps each can give the respective desired products only in such unsatisfactory yields of a level as low as about 70–80%.

In addition to pentostatin which is known to be useful for the therapy of lymphocytic leukemia, it is expectable that 2'-deoxy-2'-fluorocoformycin and epimers thereof as well as 2'-chloropentostatin, and generally, a 2'-deoxy-2'-halocoformycin and their epimers, would also be practically useful as therapeutic agents for lymphocytic leukemia and for a variety of diseases attributable to the actions of adenosine deaminase. The present inventors have now intended, therefore, to provide a new process or processes for the chemical synthesis of 2'-deoxy-2'-halocoformycins and epimers thereof by which these products can be obtained in a practically high and effective yield.

DISCLOSURE OF THE INVENTION

An object of this invention is to provide a process for the synthesis of not only 2'-deoxy-2'-fluorocoformycin which we already synthesized, but also, in general, 2'-deoxy-2'-halocoformycins in a yield practically high and acceptable.

We have accordingly made extensive investigations to achieve the above object, and as a result now have attained various findings as undermentioned. Thus, we have now found that various 3,5-di-O-lower alkanoyl or benzoyl-2-chloro- or bromo- or iodo-2-deoxy-α,β-D-ribofuranosyl or arabinofuranosyl amines can be prepared from known halo-sugar compounds by such procedures as hereinafter explained, although the 3,5-di-O-benzoyl-2-deoxy-2-fluoro-α,β-D-ribofuranosyl amine used as the starting material for the aforesaid synthesis of 2'-deoxy-2'-fluorocoformycin of the formula (B) which was already presented by us could be produced from methyl 3-deoxy-3-fluoro-β-D-allopyranoside.

Thus, we have now found that there can successfully be produced a 3,5-di-O-acyl-2-deoxy-2-halo-α,β-D-ribofuranosyl or arabinofuranosyl amine represented by the following general formula (L)

wherein A represents a hydroxyl-protecting group which is an acyl group selected from a lower alkanoyl group and benzoyl group and either one of X and Y is a hydrogen atom and the other is a halogen atom selected from fluorine, chlorine, bromine and iodine.

On the other hand, as a result of our recent study, we have now further found that there can be synthesized ethyl N-(α-tert-butoxycarbonyl-α-cyanomethyl)formimidate represented by the following formula (M)

where t-Bu represents a tertiary butyl group, with using ethyl 2-amino-2-cyanoacetate as the starting compound, although ethyl N-(α-cyano-α-ethoxycarbonylmethyl)formimidate of the above formula (G) was used as the second starting compound in the process for the preparation of 2'-deoxy-2'-fluorocoformycin of formula (B) which we already proposed (this synthetic process is explained in detail in Referential Example 1 given hereinafter).

We have further continued our investigations. As a result, we have found that generally, when a 3,5-di-O-acyl-2-deoxy-2-halo-α,β-D-ribofuranosyl or arabinofuranosyl amine of the formula (L) and ethyl N-(α-tertbutoxycarbonyl-α-cyanomethyl)formimidate of the formula (M) are heated together in a chlorinated hydrocarbon solvent, e.g. dichloroethane, under reflux, for example, for 1 hour, there takes place such a condensation reaction by which are produced a tert-butyl 1-(3,5-di-O-acyl-2-deoxy-2-halo-β-D-ribofuranosyl or arabinofuranosyl)-5-aminoimidazole-4-carboxylate represented by the following formula (II)

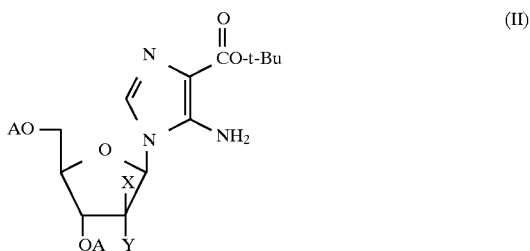

wherein A has the same meaning as defined in formula (L), X and Y also have the same meanings as defined in formula (L) and t-Bu stands for tertiary butyl group, as well as a tert-butyl 1-(3,5-di-O-acyl-2-deoxy-2-halo-α-D-ribofuranosyl or arabinofuranosyl)-5-aminoimidazole-4-carboxylate represented by the following formula (II')

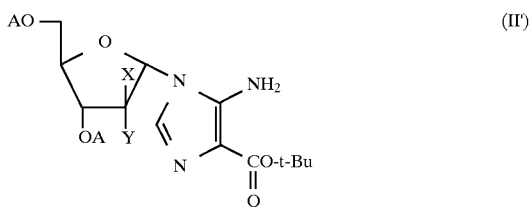

wherein A, X, Y and t-Bu are as defined above, in the form of a mixture of their β-isomer and α-isomer. We have also found that when the said mixture of β- and α-isomers so obtained is recovered and subjected to silica gel column chromatography (as developed with a solvent mixture of ethyl acetate and chloroform), the desired β-isomer of formula (II) can be recovered separately from the α-isomer of formula (II').

As a result of our further investigations, it has now been found that when there is effected the reaction of the β-isomer compound of the formula (II) in solution in N,N-dimethylformamide with an N-carboalkoxyphtalimide of the following formula (III)

where R is a lower alkyl group, preferably with N-carboethoxyphtalimide, in the presence of potassium carbonate at room temperature for about 2 hours or longer, or the reaction of the β-isomer compound (II) with phthalic anhydride in N,N-dimethylformamide in the presence of triethylamine at 50°–90° C. for 2–3 hours, a tert-butyl 1-(3,5-di-O-acyl-2-deoxy-2-halo-β-D-ribofuranosyl or arabinofuranosyl)-5-phthalimidoimidazole-4-carboxylate represented by the following formula (IV)

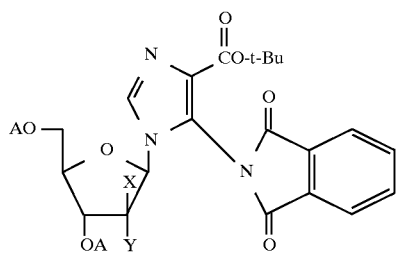

wherein A, X, Y and t-Bu are as defined above can be produced in a yield of the order of 90%.

Further, we have found that when the compound of the formula (IV) is treated with trifluoroacetic acid in dichloromethane at room temperature, effective removal of the tertiary butyl group (t-Bu) therefrom can be effected, whereby affording a 1-(3,5-di-O-acyl-2-deoxy-2-halo-β-D-ribofuranosyl or arabinofuranosyl)-5-phthalimidoimidazole-4-carboxylic acid represented by the following formula (V)

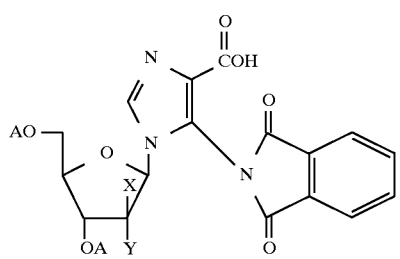

wherein A, X and Y have the same meanings as defined above; that when the 4-carboxyl group of the compound of the formula (V) is reacted with a chlorinating agent, e.g. N,N-dimethylchloroforminium chloride, to convert the 4-carboxyl group into chloroformyl group, there can be produced a 1-(3,5-di-O-acyl-2-deoxy-2-halo-β-D-ribofuranosyl or arabinofuranosyl)-4-chloroformyl-5-phthalimidoimidazole represented by the following formula (VI)

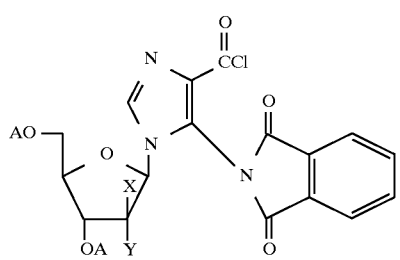

wherein A, X and Y have the same meanings as defined above; that when the compound of the formula (VI) is reacted with diazomethane, there can be produced a 1-(3,5-di-O-acyl-2-deoxy-2-halo-β-D-ribofuranosyl or arabinofuranosyl)-4-diazoacetyl-5-phthalimidoimidazole represented by the following formula (VII)

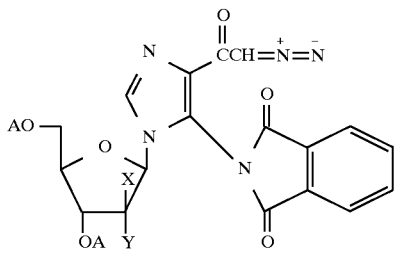

wherein A, X and Y have the same meanings as defined above.

We have further found that when the compound of the formula (VII) is reacted with hydrogen chloride in an organic solvent, there can be produced a 1-(3,5-di-O-acyl-2-deoxy-2-halo-β-D-ribofuranosyl or arabinofuranosyl)-4-chloroacetyl-5-phthalimidoimidazole represented by the following formula (VIII)

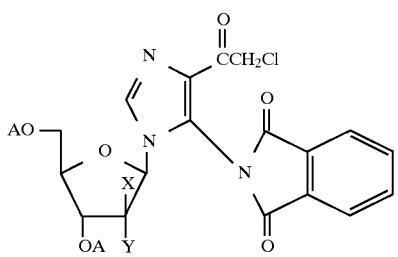

wherein A, X and Y have the same meanings as defined above; that when the compound of the formula (VIII) is treated with hydrazine to cleave the 5-phthalimido group from the compound of the formula (VIII), there can be produced a 1-(3,5-di-O-acyl-2-deoxy-2-halo-β-D-ribofuranosyl or arabinofuranosyl)-5-amino-4-chloroacetylimidazole represented by the following formula (IX)

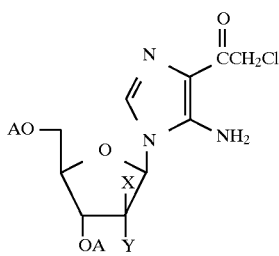

wherein A, X and Y have the same meanings as defined above; that when the compound of formula (IX) is reacted with an alkali metal azide or an alkaline earth metal azide, there can be afforded a 1-(3,5-di-O-acyl-2-deoxy-2-halo-β-D-ribofuranosyl or arabinofuranosyl)-5-amino-4-azidoacetyl-imidazole represented by the following formula (X)

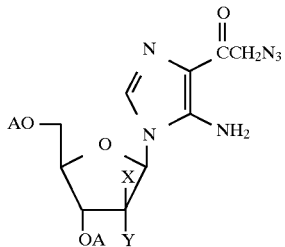

wherein A, X and Y have the same meanings as defined above; that when catalytic reduction of the 4-azidoacetyl group of the compound of formula (X) is effected with hydrogen to convert said group into an aminoacetyl group, there can be afforded a 1-(3,5-di-O-acyl-2-deoxy-2-halo-β-D-ribofuranosyl or arabinofuranosyl)-5-amino-4-aminoacetylimidazole represented by the following formula (XI)

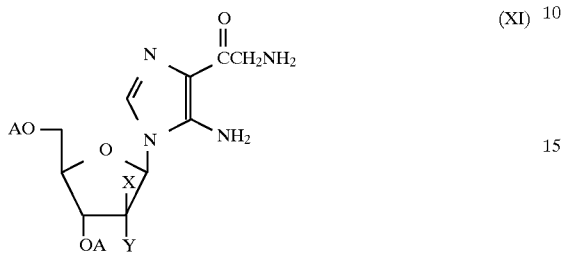

wherein A, X and Y have the same meanings as defined above; and that when the compound of formula (XI) is reacted with triethyl orthoformate of the following formula (XII)

there can be produced a 3-(3,5-di-O-acyl-2-deoxy-2-halo-β-D-ribofuranosyl or arabinofuranosyl)-6,7-dihydroimidazo[4,5-d][1,3]diazepin-8(3H)-one represented by the following formula (XIII)

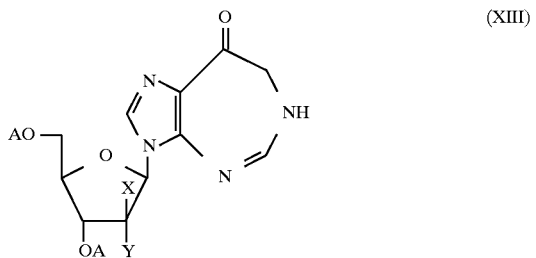

wherein A, X and Y have the same meanings as defined above.

Furthermore, we have found that when a reaction for the removal of the hydroxyl-protecting groups (A) from the compound of the formula (XIII) is carried out, there can be formed a 3-(2-deoxy-2-halo-β-D-ribofuranosyl or arabinofuranosyl)-6,7-dihydroimidazo[4,5-d][1,3]diazepin-8(3H)one represented by the following formula (XIII-a)

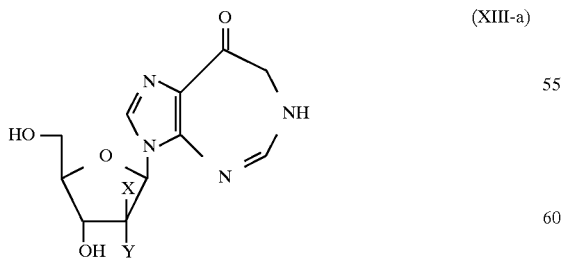

wherein A, X and Y have the same meanings as defined above; that when the compound of the formula (XIII-a) is subjected to a reduction with lithium borohydride or sodium borohydride, there can be afforded the intended product having the following formula (I-a)

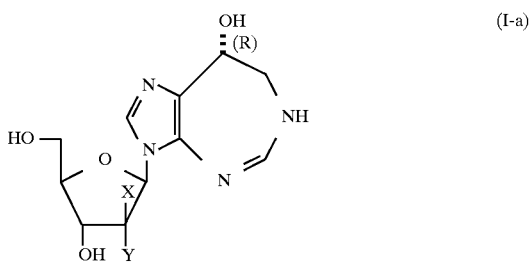

i.e. a 2'-deoxy-2'-halocoformycin [namely, the compound of general formula (I-a) where X is a hydrogen atom and Y is a halogen atom] or a 2'-deoxy-2'-epi-2'-halocoformycin [namely, the compound of general formula (I-a) where X is a halogen atom and Y is a hydrogen atom], and also the product having the following formula (I-b)

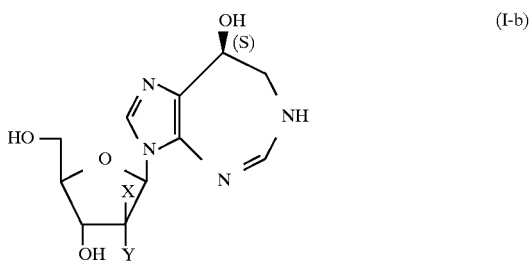

i.e. a 2'-deoxy-8-epi-2'-halocoformycin [namely, the compound of general formula (I-b) where X is a hydrogen atom and Y is a halogen atom] or a 2'-deoxy-8,2'-diepi-2'-halocoformycin [namely, the compound of general formula (I-b) where X is a halogen atom and Y is a hydrogen atom].

According to a first aspect of this invention, therefore, there is provided a process for the preparation of a 2'-deoxy-2'-halocoformycin and a 2'-deoxy-8-epi-2'-halocoformycin or stereoisomers thereof, which comprises the following steps, namely:

(1) a first step of reacting a tert-butyl 1-(3,5-di-O-acyl-2-deoxy-2-halo-5-D-ribofuranosyl or arabinofuranosyl)-5-aminoimidazole-4-carboxylate represented by the general formula (II)

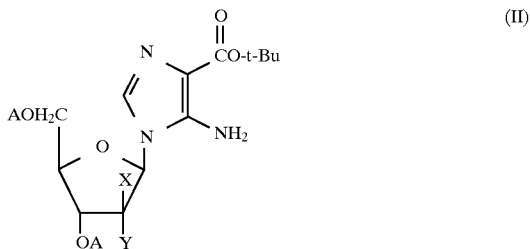

wherein A represents a hydroxyl-protecting group which is an acyl group selected from a lower alkanoyl group and benzoyl group, either one of X and Y is a hydrogen atom and the other is a halogen atom, and t-Bu is a tertiary butyl group, with an N-carboalkoxyphthalimide of the following formula (III)

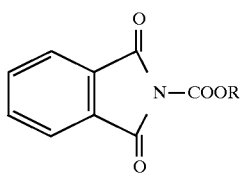

wherein R is a lower alkyl group or with phthalic anhydride to produce a tert-butyl 1-(3,5-di-O-acyl-2-deoxy-2-halo-β-D-ribofuranosyl or arabinofuranosyl)-5-phthalimidoimidazole-4-carboxylate represented by the following formula (IV)

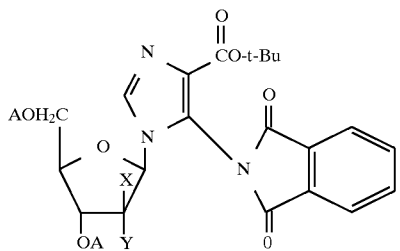

wherein A, X, Y and t-Bu have the same meanings as defined above;

(2) a second step of treating the compound of the formula (IV) with trifluoroacetic acid to remove the tertiary butyl group from the compound of the formula (IV), thereby to give a 1-(3,5-di-O-acyl-2-deoxy-2-halo-β-D-ribofuranosyl or arabinofuranosyl)-5-phthalimidoimidazole-4-carboxylic acid represented by the following formula (V)

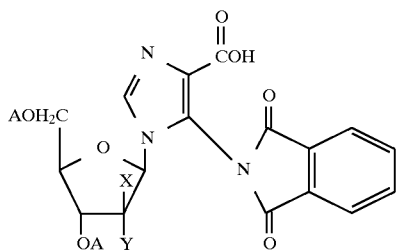

wherein A, X and Y have the same meanings as defined above;

(3) a third step of reacting the 4-carboxyl group of the compound of the formula (V) with a chlorinating agent to convert the said group into chloroformyl group, thereby to give a 1-(3,5-di-O-acyl-2-deoxy-2-halo-β-D-ribofuranosyl or arabinofuranosyl)-4-chloroformyl-5-phthalimidoimidazole represented by the following formula (VI)

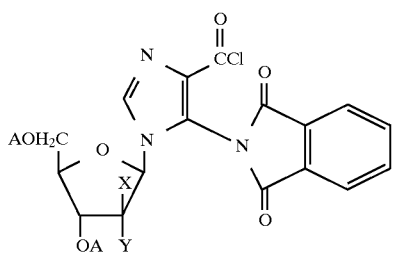

wherein A, X and Y have the same meanings as defined above;

(4) a fourth step of reacting the compound of the formula (VI) with diazomethane to give a 1-(3,5-di-O-acyl-2-deoxy-2-halo-β-D-ribofuranosyl or arabinofuranosyl)-4-diazoacetyl-5-phthalimidoimidazole represented by the following formula (VII)

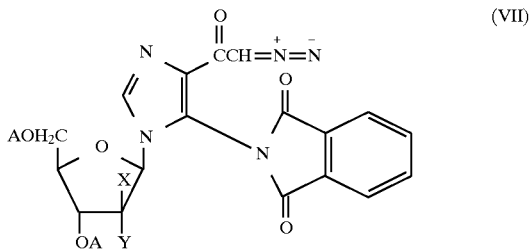

wherein A, X and Y have the same meanings as defined above;

(5) a fifth step of reacting the compound of the formula (VII) with hydrogen chloride in an organic solvent to give a 1-(3,5-di-O-acyl-2-deoxy-2-halo-β-D-ribofuranosyl or arabinofuranosyl)-4-chloroacetyl-5-phthalimidoimidazole represented by the following formula (VIII)

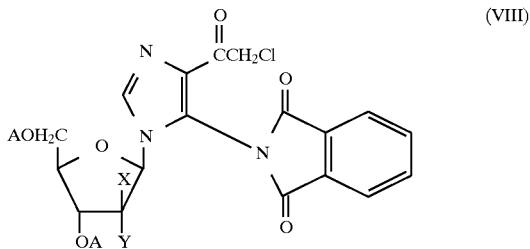

wherein A, X and Y have the same meanings as defined above;

(6) a sixth step of treating the compound of the formula (VIII) with hydrazine to cleave the 5-phthalimido group from the compound of the formula (VIII), thereby to give a 1-(3,5-di-O-acyl-2-deoxy-2-halo-β-D-ribofuranosyl or arabinofuranosyl)-5-amino-4-chloroacetylimidazole represented by the following formula (IX)

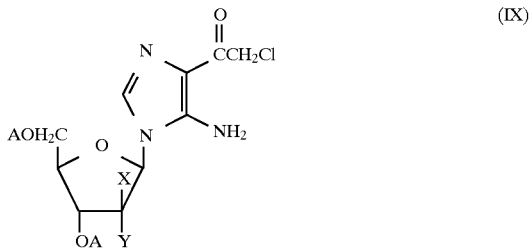

wherein A, X and Y have the same meanings as defined above;

(7) a seventh step of reacting the compound of the formula (IX) with an alkali metal azide or an alkaline earth metal azide to give a 1-(3,5-di-O-acyl-2-deoxy-2-halo-β-D-ribofuranosyl or arabinofuranosyl)-5-amino-4-azidoacetylimidazole represented by the following formula (X)

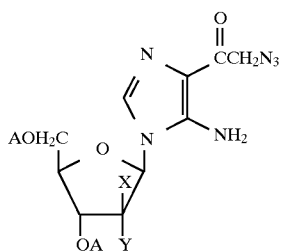

(X)

wherein A, X and Y have the same meanings as defined above;

(8) an eighth step of catalytically reducing the 4-azidoacetyl group of the compound of the formula (X) with hydrogen to convert said group into aminoacetyl group, thereby to give a 1-(3,5-di-O-acyl-2-deoxy-2-halo-β-D-ribofuranosyl or arabinofuranosyl)-5-amino-4-aminoacetylimidazole represented by the following formula (XI)

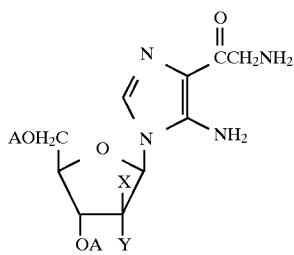

(XI)

wherein A, X and Y have the same meanings as defined above;

(9) a ninth step of reacting the compound of the formula (XI) with triethyl orthoformate of the formula (XII)

$CH(OC_2H_5)_3$                                                  (XII)

to give a 3-(3,5-di-O-acyl-2-deoxy-2-halo-β-D-ribofuranosyl or arabinofuranosyl)-6,7-dihydroimidazo[4,5-d][1,3]diazepin-8(3H)-one represented by the following formula (XIII)

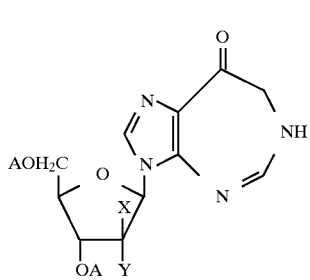

(XIII)

wherein A, X and Y have the same meanings as defined above;

(10) a tenth step of subjecting the compound of the formula (XIII) to a reaction for removal of the hydroxyl-protecting groups (A) therefrom to produce a 3-(2-deoxy-2-halo-β-D-ribofuranosyl or arabinofuranosyl)-6,7-dihydroimidazo[4,5-d][1,3]diazepin-8(3H)-one represented by the following formula (XIII-a)

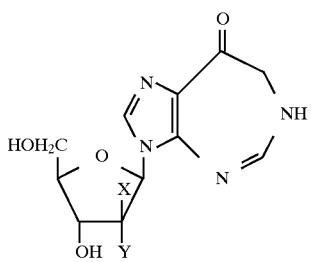

(XIII-a)

wherein A, X and Y have the same meanings as defined above; and

(11) an eleventh step of reducing the compound of the formula (XIII-a) with lithium borohydride or sodium borohydride to give a compound having the following formula (I-a)

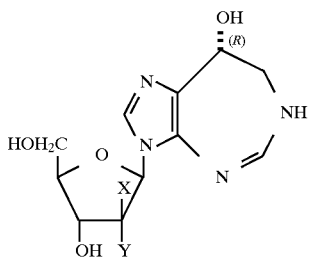

(I-a)

i.e. a 2'-deoxy-2'-halocoformycin [namely, the compound of formula (I-a) where X is a hydrogen atom and Y is a halogen atom] or a 2'-deoxy-2'-epi-2'-halocoformycin [namely, the compound of formula (I-a) where X is a halogen atom and Y is a hydrogen atom] and also a compound of the following formula (I-b)

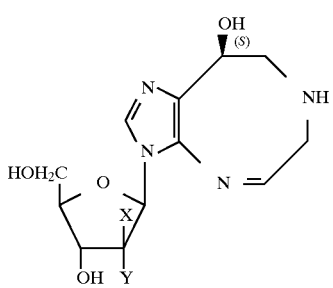

(I-b)

i.e. a 2'-deoxy-8-epi-2'-halocoformycin [namely, the compound of formula (I-b) where X is a hydrogen atom and Y is a halogen atom] or a 2'-deoxy-8,2'-diepi-2'-halocoformycin [namely, the compound of formula (I-b) where X is a halogen atom and Y is a hydrogen atom].

The process according to the first aspect of this invention, when carried out with using as the starting compound of the formula (II) tert-butyl 1-(3,5-di-O-acyl-2-deoxy-2-halo-β-D-arabinofuranosyl)-5-aminoimidazole-4-carboxylate, can give a 2'-deoxy-2'-epi-2'-halocoformycin of the following formula (I-a-1)

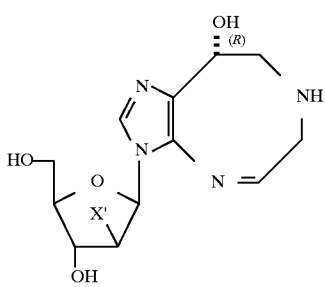

wherein X' represents a halogen atom chosen from fluorine, chlorine, bromine and iodine, and a 2'-deoxy-8,2'-diepi-2'-halocoformycin of the following formula (I-b-1)

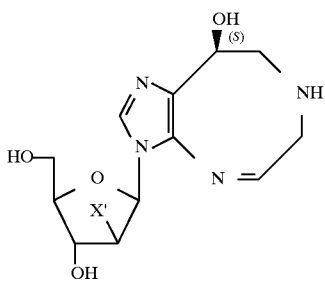

wherein X' represents a halogen atom same as above.

The process according to the first aspect of this invention, when carried out with using as the starting compound of formula (II) tert-butyl 1-(3,5-di-O-acyl-2-deoxy-2-halo-β-D-ribofuranosyl)-5-aminoimidazole-4-carboxylate, can give a 2'-deoxy-2'-halocoformycin of the following formula (I-a-2)

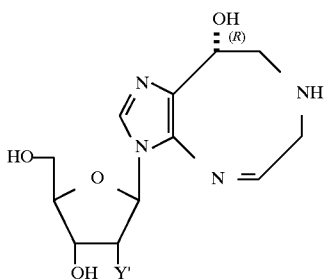

wherein Y' represents a halogen atom chosen from fluorine, chlorine, bromine and iodine, and a 2'-deoxy-8-epi-2'-halocoformycin of the following formula (I-b-2)

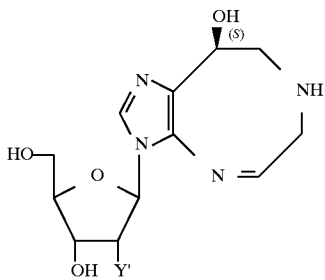

wherein Y' represents a halogen atom same as above.

Now, some details for carrying out the process according to the first aspect of this invention are disclosed.

In the first step of the process according to the first aspect of this invention, the compound of the formula (II) is reacted with an N-carboalkoxyphthalimide of the formula (III) in N,N-dimethylformamide in the presence of a base, for example, potassium carbonate at room temperature to protect the amino group of the compound of the formula (II) with phthaloyl group. Alternatively, the compound of the formula (II) may be reacted with phthalic anhydride in N,N-dimethylformamide in the presence of a lower alkylamine such as triethylamine at a temperature of 50°–90° C. for 2–3 hours. Thus, the compound of the formula (IV) can be produced.

In the second step, the compound of the formula (IV) is reacted with trifluoroacetic acid in a chlorinated hydrocarbon solvent, e.g. dichloromethane, at room temperature overnight to remove the tert-butyl group forming an ester group at the 4-side chain. Thus, the compound of the formula (V) can be produced.

In the third step, the compound of the formula (V) as dissolved in tetrahydrofuran is reacted with a chlorinating agent such as N,N-dimethylchloroforminium chloride under ice-cooling, thereby to cause a chlorination reaction so that the corresponding acid chloride of the formula (VI) is formed.

In the fourth step, the acid chloride of the formula (VI) is reacted, without being separated from the reaction solution, with diazomethane at room temperature so that the intended carbon-increasing reaction proceeds to give the diazo compound of the formula (VII).

In the fifth step, the diazo compound of the formula (VII) in a chlorinated hydrocarbon solvent, e.g. dichloromethane is reacted with hydrogen chloride in the form of a diethyl ether solution at room temperature so that the 4-diazoacetyl group of the compound of the formula (VII) is converted into the 4-chloroacetyl group to form the compound of the formula (VIII).

In the sixth step, the compound of the formula (VIII) as dissolved in a chlorinated hydrocarbon solvent, e.g. dichloromethane, is reacted with hydrazine monohydrate at 0° C. or a lower temperature to remove the phthaloyl group from the compound of the formula (VIII). Thus, the compound of the formula (IX) is produced.

In the seventh step, the compound of the formula (IX) is reacted with an alkali metal azide, e.g. sodium azide, or an alkaline earth metal azide in N,N-dimethylformamide at room temperature to convert the chloro group of the compound of the formula (IX) into an azido group. Thus, the compound of the formula (X) is produced.

In the eighth step, the compound of the formula (X) is reacted with hydrogen in methanol in the presence of a hydrogenation catalyst, such as palladium black at room temperature to catalytically reduce the azido group of the compound of formula (X) into amino group. Thus, the compound of the formula (XI) is produced.

In the ninth step, the compound of the formula (XI) as dissolved in N,N-dimethylformamide is reacted with triethyl orthoformate of the formula (XII) at room temperature to cause the formation of the 1,3-diazepine ring. Thus, the compound of the formula (XIII) is produced.

In the tenth step, the compound of the formula (XIII) is treated in a sodium methylate-methanolic solution at room temperature to effect the reaction for removal of the hydroxyl-protecting acyl groups from the sugar moiety of the compound of the formula (XIII). Thus, the compound of the formula (XIII-a) is afforded.

In the eleventh step, the compound of the formula (XIII-a) as dissolved in aqueous methanol is treated with a metal borohydride, e.g. lithium borohydride or sodium borohydride at room temperature so that the 8-oxo group at the diazepine ring of the compound of the formula (XIII-a) is reduced into a hydroxyl group. Thus, there are obtained as the desired final products a 2'-deoxy-2'-halocoformycin and a 2'-deoxy-8-epi-2'-halocoformycin, or alternatively a 2'-deoxy-2'-epi-2'-halocoformycin and a 2'-deoxy-8,2'-diepi-2'-halocoformycin.

In the process according to the first aspect of this invention, the overall yield of the total of the target product of the general formula (I-a) and the target product of the general formula (I-b) can reach 40–50% of the theoretical yield as calculated on the starting compound of the formula (II).

According to a second aspect of this invention, there is provided as a novel compound a tert-butyl 1-(3,5-di-O-acetyl or benzoyl-2-deoxy-2-halo-β-D-ribofuranosyl or arabinofuranosyl)-5-aminoimidazole-4-carboxylate of the general formula (II-a)

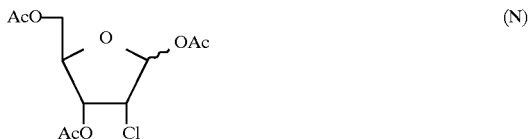

wherein either one of X and Y is a hydrogen atom and the other is a halogen atom, A' is acetyl group or benzoyl group, t-Bu is tertiary-butyl group, which is to be used as the starting compound in the process according to the first aspect of this invention.

According to a third aspect of this invention, there is provided as a novel compound a tert-butyl 1-(3,5-di-O-acetyl or benzoyl-2-deoxy-2-halo-β-D-ribofuranosyl or arabinofuranosyl)-5-phthalimidoimidazole-4-carboxylate of the general formula (IV-a)

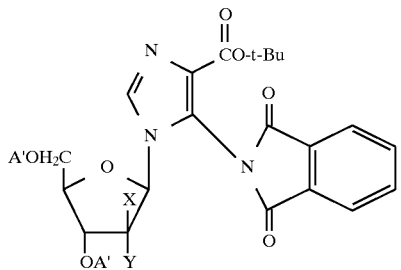

wherein either one of X and Y is a hydrogen atom and the other is a halogen atom, A' is acetyl group or benzoyl group, t-Bu is tertiary-butyl group, which is produced as the product in one reaction stage of the process according to the first aspect of this invention and which is useful as an intermediate material for the synthesis of the desired 2'-deoxy-2'-halocoformycins.

The preparation of the compound of the formula (II) or (II-a) to be used as the starting compound in the process according to the first aspect of this invention may be carried out, as above-mentioned, by reacting a 3,5-di-O-acyl-2-deoxy-2-halo-α,β-D-ribofuranosyl or arabinofuranosyl amine of the formula (L) above with the compound of the formula (M) above. Among the halo-sugar amines of the formula (L), a 3,5-di-O-acyl-2-deoxy-2-fluoro-α,β-D-ribofuranosyl or arabinofuranosyl amine may be prepared in the same manner as in the method for the preparation of 3,5-di-O-benzoyl-2-deoxy-2-fluoro-α,β-D-ribofuranosyl amine and 3,5-di-O-benzoyl-2-deoxy-2-fluoro-α,β-D-arabinofuranosyl amine as described in the above-mentioned PCT International Laid-Open publication WO93/10137 of the PCT/JP92/01489 application.

Among the halo-sugar amines of the formula (L), a 3,5-di-O-acyl-2-deoxy-2-chloro- or bromo- or iodo-α,β-D-ribofuranosyl or arabinofuranosyl amine may be prepared by the processes (a), (b) and (c) explained below.

(a) Preparation of 3,5-di-O-acetyl-2-chloro-2-deoxy-α,β-D-ribofuranosyl amine 3,5-Di-O-acetyl-2-chloro-2-deoxy-α,β-D-ribofuranosyl acetate (the compound described by J. P. Schaumberg et al., in "J. Org. Chem.," 50, pp. 1651–1656, 1985) represented by the following formula (N)

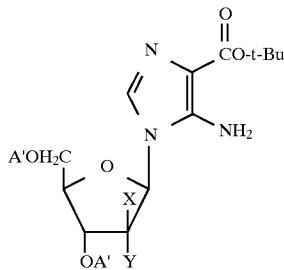

where Ac is acetyl group is dissolved in dichloromethane. To the resulting solution is added 30% hydrogen bromide in acetic acid to effect the reaction at room temperature overnight. The resulting reaction solution is concentrated and the remaining acetic acid is removed by azeotropic distillation with toluene, to yield 3,5-di-O-acetyl-2-chloro-2-deoxy-α,β-D-ribofuranosyl bromide [compound (O)] as a syrup.

Compound (O) thus obtained is then reacted with an alkali metal azide, e.g. sodium azide in acetonitrile or other suitable organic solvent in the presence of tetraethylammonium bromide at room temperature to convert the 1-bromo group of the compound (O) into azido group. Thus, there is formed a mixture of 3,5-di-O-acetyl-2-chloro-2-deoxy-α-D-ribofuranosyl azide and the β-isomer thereof.

The mixture of α- and β-isomers so obtained is reacted with hydrogen in dioxane at room temperature in the presence of a hydrogenation catalyst, e.g. palladium black to catalytically reduce the azido group of the resulting azido sugar into amino group. Thus, there is obtained 3,5-di-O-acetyl-2-chloro-2-deoxy-α,β-D-ribofuranosyl amine.

(b) Preparation of 3,5-di-O-acetyl-2-bromo- or iodo-2-deoxy-α,β-D-ribofuranosyl amine 2-Bromo- or iodo-2-deoxy-β-D-ribofuranose (the compound described by I. V. Il'icheva et al., in "Bioorg. Khim.", 15, pp. 800–815, 1989) and "Chemical Abstracts", 112, 77730b] represented by the following formula (P)

is dissolved in pyridine. To the resulting solution is added acetic anhydride under ice-cooling and the resultant mixture is allowed to stand overnight at room temperature. The reaction solution obtained is concentrated and the resulting syrup is extracted with chloroform. The chloroform extract so separated is washed with water, dried and then concentrated, to afford 3,5-di-O-acetyl-2-bromo- or iodo-2-deoxy-α,β-D-ribofuranosyl acetate [compound (Q)].

Compound (Q) is reacted with 30% hydrogen bromide in acetic acid in dichloromethane at room temperature overnight to convert the 1-acetoxy group of compound (Q) into bromo group, thus affording 3,5-di-O-acetyl-2-bromo- or iodo-2-deoxy-α,β-D-ribofuranosyl bromide [compound (R)].

Compound (R) is reacted with a metal azide in the same manner as in process (a) above to convert the 1-bromo group of compound (R) into azido group, thus giving 3,5-di-O-acetyl-2-bromo- or iodo-2-deoxy-α,β-D-ribofuranosyl azide [compound (S)]. Compound (S) is then catalytically reduced with hydrogen in dioxane in the presence of palladium black in the same manner as in process (a) above to convert the 1-azido group into an amino group. Thus, there is afforded 3,5-di-O-acetyl-2-bromo or iodo-2-deoxy-α,β-D-ribofuranosyl amine.

(c) Preparation of 3,5-di-O-acyl-2-chloro- or bromo-2-deoxy-α,β-D-arabinofuranosyl amine 3,5-di-O-acetyl or 3-O-acetyl-5-O-benzoyl-2-chloro or bromo-2-deoxy-α,β-D-arabinofuranosyl bromide (the compound described by K. A. Watanabe et al., in "J. Med. Chem", 26, pp. 152–156, 1983) represented by the following formula (T)

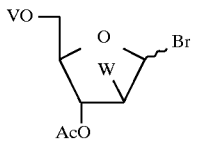

where V is acetyl or benzoyl group and W is a chlorine or bromine atom, is reacted with an alkali metal azide in acetonitrile in the same manner as in process (a) above, to form the corresponding azido sugar. The resulting azido sugar is then catalytically reduced with hydrogen in dioxane in the presence of palladium black in the same manner as in process (a) above, to afford the corresponding 3,5-di-O-acyl-2-chloro- or bromo-2-deoxy-α,β-D-arabinofuranosyl amine.

With respect to the preparation of ethyl N-(α-tert-butoxycarbonyl-α-cyanomethyl)formimidate of the formula (M) which is to be used as the other starting material for the preparation of the starting compound of the formula (II), Referential Example 1 given hereinafter is referred to.

Now, this invention is further illustrated with reference to the following Examples and Referential Examples, but it is to be understood that this invention is in no way limited to those Examples. Referential Example 1 illustrates the preparation of the compound of formula (M), Referential Examples 2–4 concretely illustrate the preparation of some halo-sugar amines valuable for the synthesis of the starting compound of formula (II) above and Examples 1–4 exemplify the detailed procedures of the process of the first aspect of this invention.

REFERENTIAL EXAMPLE 1

Preparation of ethyl N-(α-tert-butoxycarbonyl-α-cyanomethyl)formimidate [compound of formula (M)]

(1) Synthesis of ethyl 2-benzyloxycarbonylamino-2-cyanoacetate [Compound (2)]

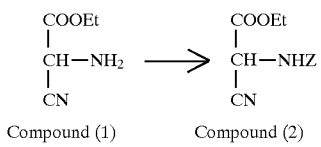

wherein Et denotes ethyl group and Z denotes benzyloxycarbonyl group; the same abbreviations apply to hereinafter.

Ethyl 2-amino-2-cyanoacetate [compound (1)] (refer to G. Shaw and D. V. Wilson, "J. Chem. Soc.", pp. 2937–2943, 1962; and F. I. Logemann and G. Shaw, "Chemistry and Industry", 5, p. 542, 1980)(200 mg) was dissolved in a mixture (4 ml) of dioxane-water (1:1). To the resulting solution was added benzyloxycarbonyl chloride (0.27 ml) and the mixture obtained was allowed to react at room temperature for 1 hour, thereby to protect the amino group of compound (1) with benzyloxycarbonyl group.

The reaction solution was concentrated and the resulting syrup was extracted with chloroform. The chloroform extract was washed with water, dried over anhydrous sodium sulfate and concentrated to leave a colorless solid. The solid was crystallized from chloroform-n-hexane, to afford the titled compound (2) as colorless crystals (287 mg). Yield: 70% mp: 115°–116° C.

$^1$H-NMR spectrum (in deutero-chloroform, TMS as the internal standard)

δ1.36 (3H, t, CH$_2$CH$_3$)

4.36 (2H, q, CH$_2$CH$_3$)

5.18 (2H, s, CH$_2$C$_6$H$_5$)

7.37 (5H, s, CH$_2$C$_6$H$_5$)

Elemental analysis: Found: C 59.45%, H 5.32%, N 10.69% Calculated for C$_{13}$H$_{14}$N$_2$O$_4$ C 59.54%, H 5.38%, N 10.68%

(2) Synthesis of 2-benzyloxycarbonylamino-2-cyanoacetic acid [Compound (3)]

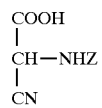

The compound (2) obtained in step (1) above (1.1 g) was dissolved in dioxane (15 ml). To the solution was added a 0.5M aqueous sodium hydroxide solution (21 ml), and the resulting mixture was allowed to react at room temperature for 1 hour, so that the ester-forming ethyl group of compound (2) was removed therefrom by hydrolysis. After water (100 ml) was added to the reaction solution as diluent, the resultant solution was neutralized with 1M hydrochloric acid under ice-cooling so as to make the solution acidic (pH 2). The acidic solution was extracted with ethyl acetate and the extract was dried over anhydrous sodium sulfate and concentrated to obtain the titled compound (3) as a colorless solid (960 mg). Yield: 98%

Elemental analysis: Found: C 56.46%, H 4.38%, N 11.96% Calculated for C$_{11}$H$_{10}$N$_2$O$_4$ C 56.41%, H 4.30%, N 11.96%

(3) Synthesis of tert-butyl 2-benzyloxycarbonylamino-2-cyanoacetate [Compound (4)]

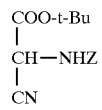

Compound (3) obtained in step (2) above (486 mg) was dissolved in a mixture (12 ml) of benzene-tert-butyl alcohol (5:1). To the resulting solution was added trifluoroacetic anhydride (1.2 ml) and the mixture obtained was allowed to react at room temperature for 0.5 hours under stirring to esterify the carboxyl group of compound (3) with the tert-butyl group.

The reaction solution was neutralized with a 10% aqueous sodium hydroxide solution (4.5 ml) added and the organic layer separated was washed with water, dried over anhydrous sodium sulfate and concentrated to leave a yellow syrup. The syrup was purified by silica gel column chromatography (developer solvent: n-hexane-chloroform-ethyl acetate, 4:2:1), to obtain the titled compound (4) as colorless solid (477 mg). Yield: 79%.

$^1$H-NMR spectrum (in deutero-chloroform, TMS as the internal standard)

δ1.53 [9H, s, C(CH$_3$)$_3$]

7.37 (5H, s, $\underline{CH_2C_6H_5}$

Elemental analysis: Found: C 61.88%, H 6.38%, N 9.65%
Calculated for $C_{15}H_{18}N_2O_4$ C 62.06%, H 6.25%, N 9.65%

(4) Synthesis of tert-butyl 2-amino-2-cyanoacetate [Compound (5)]

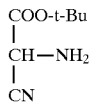

Compound (5)

Compound (4) obtained in step (3) above (3.10 g) was dissolved in dioxane (90 ml) and acetic acid (0.70 ml) was added thereto. Hydrogen was blown into the resulting mixture at room temperature in the presence of palladium black as catalyst for 5 hours to effect catalytic reduction, thus eliminating the benzloxycarbonyl group from compound (4).

The reaction solution was filtered and the filtrate was concentrated to leave a syrup, which was then extracted with chloroform. The extract was washed with a 5% aqueous sodium hydrogen carbonate solution, dried over anhydrous sodium sulfate and concentrated to afford the titled compound (5) as an unstable and syrupy substance (1.45 g). Yield: 87%.

(5) Synthesis of ethyl $\underline{N}$-($\alpha$-tert-butoxycarbonyl-$\alpha$-cyanomethyl) of formula (M) [Compound (6)]

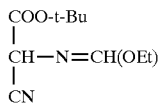

Compound (6)

Compound (5) obtained in step (4) above (290 mg) was dissolved in dichloroethane (6 ml), to which was then added triethyl orthoformate (0.01 ml). The mixture obtained was heated under reflux for 1 hour to effect the condensation reaction intended. The reaction solution was concentrated to obtain the titled compound (6) as an unstable and syrupy substance (355 mg). Yield: 90% .

$^1$H-NMR spectrum (in deutero-chloroform, TMS as the internal standard)
$\delta$1.33 (3H, t, $\underline{CH_2CH_3}$)
1.52 [9H, s, $C(C\underline{H_3})_3$]
4.25 (2H, q, $\underline{CH_2}CH_3$)
4.87 (1H, s, $>\underline{CH}$—N)
7.78 (1H, s, N=CH—)

REFERENTIAL EXAMPLE 2

Synthesis of 3,5-di-O-benzoyl-2-deoxy-2-fluoro-$\alpha$,$\beta$-D-arabinofuranosyl amine [Compound (8)]

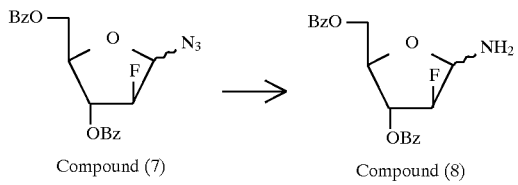

Compound (7)   Compound (8)

wherein Bz denotes benzoyl group (the same abbreviation applies to hereinafter).

3.5-Di-O-benzoyl-2-deoxy-2-fluoro-$\alpha$,$\beta$-D-arabinofuranosyl azide [compound (7)] (see Example 2 of PCT International Laid-Open publication WO 93/10137 specification of PCT/JP 92/01489 application) in the form of a colorless syrup (350 mg) was dissolved in dioxane (7 ml). Into this solution, hydrogen was blown at room temperature in the presence as catalyst of palladium black for 1 hour to conduct the catalytic reduction intended, thereby convert the azido group of compound (7) into amino group. The reaction solution obtained was filtered and the filtrate was concentrated up to about a half volume thereof, and then diluted with dichloroethane (50 ml). The diluted solution was dried over calcium chloride, and then a small amount of triethylamine was added thereto, followed by concentration to afford the titled compound (8) as a colorless syrup (324 mg). Crude yield: 99%.

EXAMPLE 1

Preparation of 2'-deoxy-2'-epi-2'-fluorocoformycin and 2'-deoxy-8,2'-diepi-2'-fluorocoformycin (1) Synthesis of tert-butyl 5-amino-1-(3,5-di-O-benzoyl-2-deoxy-2-fluoro-$\alpha$ and $\beta$-D-arabinofuranosyl)imidazole-4-carboxylates[Compound (10) and Compound (9)]

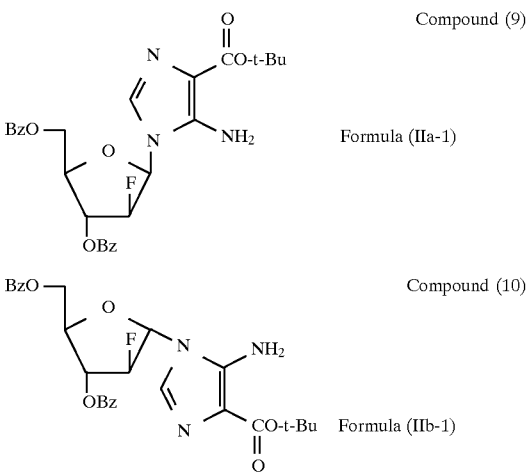

The syrup of compound (8) obtained in Referential Example 2 was dissolved in dichloroethane (7 ml), to which was then added a solution in dichloroethane (7 ml) of compound (6) (350 mg) [the compound of formula (M)] as obtained in Referential Example 1. The resulting mixture was heated under reflux for 1 hour to conduct the reaction intended. Thus, there occurred the aminoimidazolation reaction of compound (8) to produce compound (9) and compound (10).

The resulting reaction solution containing these compounds was concentrated and the resulting syrup was subjected to silica gel column chromatography (developer solvent: chloroform-ethyl acetate, 5:1) for isolation and purification of the desired products. Thus, there were obtained the titled compound (9) as a colorless solid (105 mg) and compound (10) as colorless crystals (82 mg). The yields of compound (9) and compound (10) as calculated on the basis of compound (7) were 22% and 17%, respectively.
Compound (9) ($\beta$-isomer)
$[\alpha]_D^{25}$ -24° (c 1, chloroform)
$^1$H-NMR spectrum (in deutero-chloroform, TMS as the internal standard)
$\delta$1.58 [9H, s, $C(CH_3)_3$]
5.24 (2H, br s, $NH_2$)
5.37 (1H, ddd, H-2')
5.89 (1H, dd, H-1')
$J_{1',2'}$=2.5, $J_{1',F}$=23, $J_{2',F}$=50 Hz
$^{19}$F-NMR spectrum (in deutero-chloroform, Freon 11 as the internal standard)
$\delta$-198.4 (dddd)
Elemental analysis Found: C 61.89%, H 5.61%, F 3.40%, N 8.16% Calculated for $C_{27}H_{28}FN_3O_7$ C 61.71%, H 5.37%, F 3.62%, N 8.00%

Compound (10) (α-isomer)
  mp: 227°–228° C.
  $[α]_D^{23}$ +40° (c 1, chloroform)
  $^1$H-NMR spectrum (in deutero-chloroform, TMS as the internal standard)
  δ1.60 [9H, s, C(CH$_3$)$_3$]
  5.16 (2H, S, NH$_2$)
  5.77 (1H, dt, H-2')
  6.04 (1H, dd, H-1')
  $J_{1',2'}$=2, $J_{1',F}$=16, $J_{2',F}$=49.5 Hz
  $^{19}$F-NMR spectrum (in deutero-chloroform, Freon 11 as the internal standard)
  δ–187.7 (ddd)
  Elemental analysis Found: C 61.77%, H 5.53%, F 3.48%, N 8.18% Calculated for C$_{27}$H$_{28}$FN$_3$O$_7$ C 61.71%, H 5.37%, F 3.62%, N 8.00%

(2) Synthesis of tert-butyl 1-(3,5-di-O-benzoyl-2-deoxy-2-fluoro-β-D-arabinofuranosyl)-5-phthalimidoimidazole-4-carboxylate [Compound (11)]

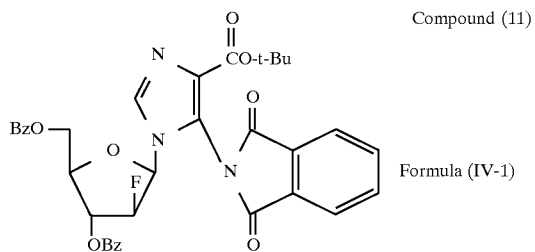

Compound (11)
Formula (IV-1)

was dissolved in N,N-dimethylformamide (6 ml). To the solution were added potassium carbonate (118 mg) and N-carboethoxyphthalimide (175 mg), and the resutant mixture was stirred at room temperature for 2 hours to conduct the reaction intended, to afford compound (11) above.

The react ion solution was filtered and the filtrate was concentrated to leave a syrup, which was then purified by silica gel column chromatography (developer solvent: toluene-ethyl acetate, 2:1), to afford the titled compound (11) as a colorless solid (453 mg). Yield: 92%.

$^1$H-NMR spectrum (in deutero-chloroform, TMS as the internal standard)
δ1.35 [9H, s, C(CH$_3$)$_3$]
5.30 (1H, ddd, H-2')

(3) Synthesis of 1-(3,5-di-O-benzoyl-2-deoxy-2-fluoro-β-D-arabinofuranosyl)-5-phthalimidoimidazole-4-carboxylic acid [Compound (12)]

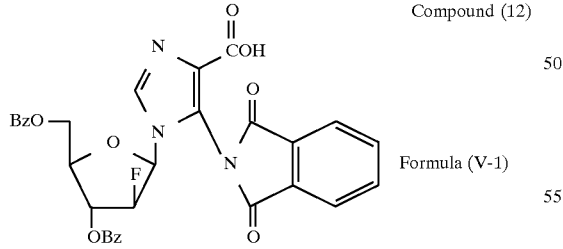

Compound (12)
Formula (V-1)

Compound (11) obtained in step (2) above (2.00 g) was dissolved in a mixture (30 ml) of trifluoroacetic acid-dichloromethane (1:4) and the resulting solution was kept overnight at room temperature, when the deesterification of compound (11) occurred. The reaction solution was concentrated and the solid obtained was washed with diethyl ether to yield the titled compound (12) (1.77 g) which was insoluble in diethyl ether. Yield: 97%.

(4) synthesis of 1-(3,5-di-O-benzoyl-2-deoxy-2-fluoro-β-D-arabinofuranosyl)-4-chloroformyl-5-phthalimidoimidazole [Compound (13)]

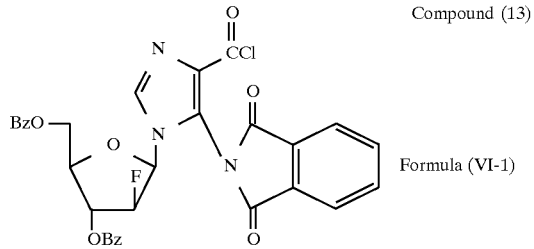

Compound (13)
Formula (VI-1)

Compound (12) obtained in step (3) above (200 mg) was dissolved in tetrahydrofuran (2 ml), to which was then added N,N-dimethylchloroforminium chloride (98 mg) under ice-cooling, and the resultant mixture was allowed to react at the same temperature for 0.5 hours. There occurred chlorination of the carboxyl group of compound (12) to give a reaction solution containing the titled Compound (13).

(5) Synthesis of 1-(3,5-di-O-benzoyl-2-deoxy-2-fluoro-β-D-arabinofuranosyl)-4-diazoacetyl-5-phthalimidoimidazole [Compound (14)]

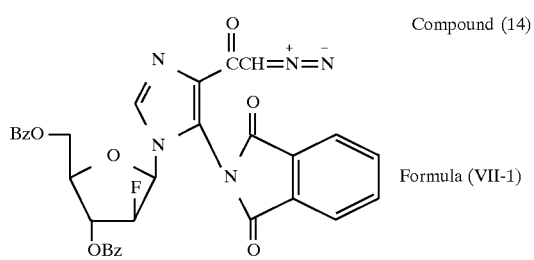

Compound (14)
Formula (VII-1)

The reaction solution containing compound (13) obtained in step (4) above as a whole was added to a 0.2M diazomethane-diethyl ether solution (30 ml). The resultant mixture was allowed to react at room temperature for 0.5 hours, so that diazomethylation of compound (13) occurred to give a reaction solution containing compound (14) above. The reaction solution obtained was concentrated to afford a solid containing compound (14).

(6) Synthesis of 1-(3,5-di-O-benzoyl-2-deoxy-2-fluoro-β-D-arabinofuranosyl)-4-chloroacetyl-5-phthalimidoimidazole [Compound (15)]

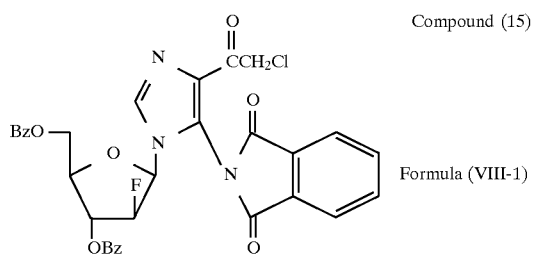

Compound (15)
Formula (VIII-1)

The solid containing compound (14) obtained in step (5) above was dissolved in dichloromethane (5 ml), to which was then added a 1M hydrogen chloride-diethyl ether solution (0.5 ml), and the resultant mixture was allowed to react for 0.5 hours to produce the titled compound (15). The reaction solution so obtained was diluted with dichloromethane and washed with water, and the organic layer obtained was dried over anhydrous sodium sulfate and then concentrated to yield the titled compound (15) as a solid (190 mg). Yield from compound (12): 90%.

$^1$H-NMR spectrum (in deutero-chloroform, TMS as the internal standard)
δ4.87 (2H, ABq, COCH$_2$Cl)

(7) Synthesis of 5-amino-1-(3,5-di-O-benzoyl-2-deoxy-2-fluoro-β-D-arabinofuranosyl)-4-chloroacetylimidazole [Compound (16)]

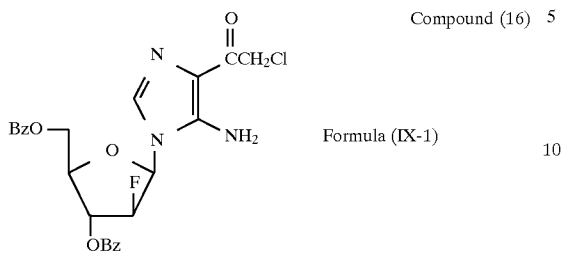

Compound (16)
Formula (IX-1)

Compound (15) obtained in step (6) above (220 mg) was dissolved in dichloromethane (9 ml), to which was then added hydrazine monohydrate (0.02 ml) under cooling at 0° C., and the resultant mixture was allowed to effect the reaction under stirring at the same temperature for 1 hour to produce the titled compound (16). The reaction solution obtained was filtered and the filtrate was concentrated to leave a solid. The solid was purified by silica gel column chromatography (developer solvent:toluene-ethyl acetate, 1:1), to afford the titled compound (16) as a colorless solid (166 mg). Yield: 95%.

(8) Synthesis of 5-amino-4-azidoacetyl-1-(3,5-di-O-benzoyl-2-deoxy-2-fluoro-β-D-arabinofuranosyl)imidazole [Compound (17)]

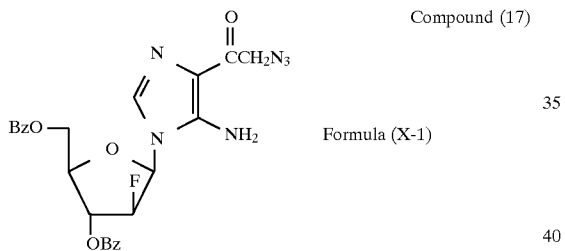

Compound (17)
Formula (X-1)

Compound (16) obtained in step (7) above (185 mg) was dissolved in N,N-dimethylformamide (3.7 ml), to which was then added sodium azide (37 mg), and the resultant mixture was stirred at room temperature for 1 hour to effect the desired reaction in order to convert the chloro group of compound (16) into azido group and thus to produce the titled compound (17). The reaction solution was concentrated and the residue obtained was extracted with ethyl acetate. The extract was washed with water and dried over anhydrous sodium sulfate and then concentrated to yield a yellow syrup. This syrup was purified by silica gel column chromatography (developer solvent:toluene-ethyl acetate, 1:1), to give the titled compound (17) as a colorless solid (176 mg). Yield: 94%.

Infrared absorption spectrum (KBr disk): 2110 cm$^{-1}$ (N$_3$)

$^1$H-NMR spectrum (in deutero-chloroform, TMS as the internal standard)

δ4.43 (2H, s, COCH$_2$N$_3$)
5.38 (1H, ddd, H-2')
6.02 (2H, slightly br s, NH$_2$)
7.14 (1H, d, H-2)

(9) Synthesis of 5-amino-4-aminoacetyl-1-(3,5-di-O-benzoyl-2-deoxy-2-fluoro-β-D-arabinofuranosyl)imidazole [Compound (18)]

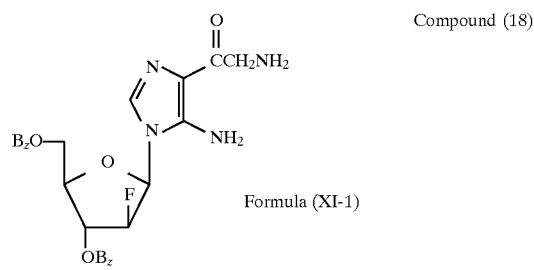

Compound (18)
Formula (XI-1)

Compound (17) obtained in step (8) above (567 mg) was dissolved in methanol (23 ml), to which was then added a 2.2M hydrogen chloride-methanol solution (0.75 ml). The resulting solution was subjected to a catalytic reduction by blowing hydrogen into the solution at room temperature in the presence as catalyst of palladium black for 1 hour (for the reduction of the azido group). The reaction solution so obtained was filtered and the filtrate was concentrated to leave a solid, which was then washed with diethyl ether, to afford the titled compound (18) as a solid (508 mg) which was insoluble in ethyl ether.

(10) Synthesis of 3-(3,5-di-O-benzoyl-2-deoxy-2-fluoro-β-D-arabinofuranosyl)-6,7-dihydroimidazo[4,5-d][1,3]diazepin-8(3H)-one [Compound (19)]

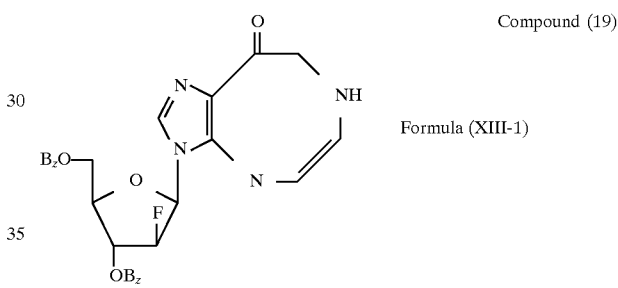

Compound (19)
Formula (XIII-1)

Compound (18) obtained in step (9) above (508 mg) was dissolved in N,N-dimethylformamide (9.4 ml), to which was then added triethyl orthoformate (2,3 ml), and the resultant mixture was allowed to effect the reaction at room temperature for 6 hours. Thus, there occurred the formation of 1,3-diazepinone ring to give compound (19) above. The resulting reaction solution containing compound (19) was neutralized by addition of triethylamine (0.2 ml) and then concentrated. The residue obtained was washed with diethyl ether to give a pale yellow solid. The solid was crystallized from methanol-acetonitrile, thus affording compound (19) (432 mg). The yield from compound (17) was 79%.

(11) Synthesis of 3-(2-deoxy-2-fluoro-β-D-arabinofuranosyl)-6,7-dihydroimidazo[4,5-d][1,3]diazepin-8(3H)-one [Compound (20)]

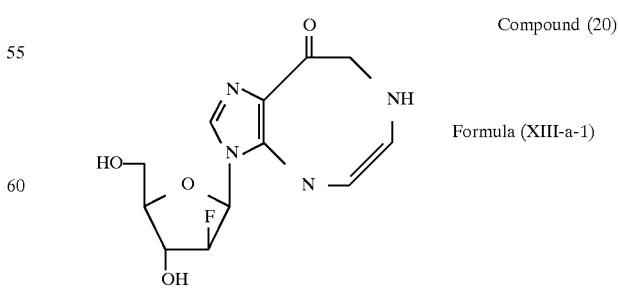

Compound (20)
Formula (XIII-a-1)

To a suspension in methanol (4 ml) of compound (19) (100.5 mg) as obtained in step (10) above was added a 0.5M sodium methylate-methanol solution (0.6 ml). The resultant mixture was stirred at room temperature for 1 hour to conduct the intended reaction. Thus, the debenzoylation of compound (19) occurred to produce the titled compound (20).

The resulting homogeneous reaction solution containing compound (20) was neutralized by addition of an ion-exchange resin, Amberlite CG-120 (H⁺-cycle) (100–200 mesh). After filtration, the filtrate was concentrated and the residual syrup was washed with diethyl ether. The diethyl ether-insoluble solid obtained was purified by silica gel column chromatography (developer solvent:chloroform-menthanol, 3:1), to afford the titled compound (20) as colorless crystals (53.4 mg). Yield: 92%.

$^1$H-NMR spectrum (in deutero-dimethylsulfoxide, TMS as the internal standard)
δ3.79 (2H, d, COCH$_2$)
5.05 (1H, dt, H-2')
6.32 (1H, dd, H-1')
7.46 (1H, d, H-5)
7.73 (1H, d, H-2)
(12) Synthesis of 2'-deoxy-2'-epi-2'-fluorocoformycin [Compound (21)] and 2'-deoxy-8,2'-diepi-2'-fluorocoformycin [Compound (22)]

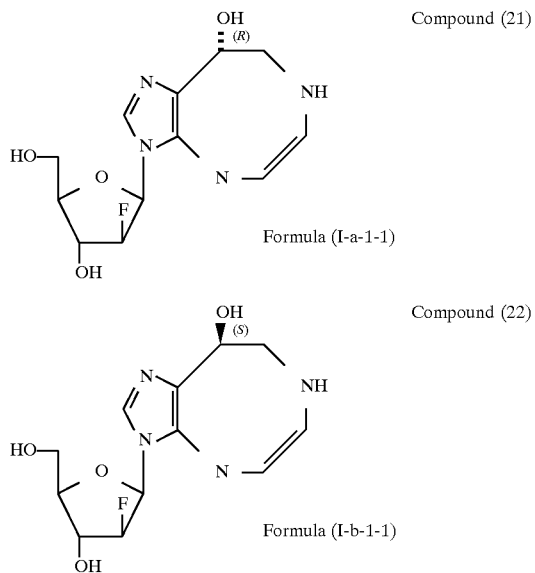

Compound (20) obtained in step (11) above (51 mg) was dissolved in a mixture (2 ml) of methanol-water (1:1), to which was then added lithium borohydride.(2.0 mg) (or sodium borohydride, 3.5 mg). The resultant mixture was allowed to effect the reduction at room temperature for 1 hour, thereby to convert the 8-oxo group of compound (20) into hydroxyl group.

To the resulting reaction solution containing compound (21) and compound (22) thus produced, was added dry ice to decompose the excess reagent, after which said solution was subjected, as such, to preparative high pressure liquid chromatography with using a reversed phase column (Senshu Pak. ODS-H-5251) (mobile phase: methanol-water, 1:9), for isolation and purification of the products. The elution was then effected in the order of compound (22) and then compound (21). Each of the eluates was concentrated, thereby to afford the titled compound (21) as colorless crystals (25 mg, yield: 49%) and the titled compound (22) as colorless crystals (23 mg, yield: 45%)
Compound (21): $[\alpha]_D^{27}$+118° (c 0.05, water)
Compound (22): $[\alpha]_D^{27}$–27° (c 0.1, water)

Compound (21) can be obtained in a yield of 26% of the theoretical yield as calculated from the starting compound (9).

EXAMPLE 2

Preparation of 2'-deoxy-2'-fluorocoformycin and 2'-deoxy-8-epi-2'-fluorocoformycin 3,5-Di-O-benzoyl-2-deoxy-2-fluoro-α,β-D-ribofuranosyl amine [compound (23)] (as prepared by the process described in Example 1 of the International Laid-Open publication WO 93/10137 of PCT Application, PCT/JP 92/01489) in the form of a colorless syrup (480 mg) was dissolved in dichloroethane (10 ml). To the resultant solution was added a solution in dichloroethane (10 ml) of compound (6) as prepared in Reference Example 1 [compound of formula (M)] (500 mg). The resultant mixture was heated under reflux for 1 hour to effect the reaction intended.

Thus, there were produced tert-butyl 5-amino-1-( 3,5-di-O-benzoyl-2-deoxy-2-fluoro-β-D-ribofuranosyl)imidazole-4-carboxylate [compound (24)] and α-isomer thereof [compound (25)] which were obtained in the form of the reaction solution containing them. The reaction solution was subjected to chromatography in the same manner as in step (1) of Example 1, thus affording compound (24) (147 mg).

Thereafter, compound (24) so obtained was processed in the same manner as in steps (2)–(12) of Example 1 to produce 2'-deoxy-2'-fluorocoformycin [compound (26)] having the following formula

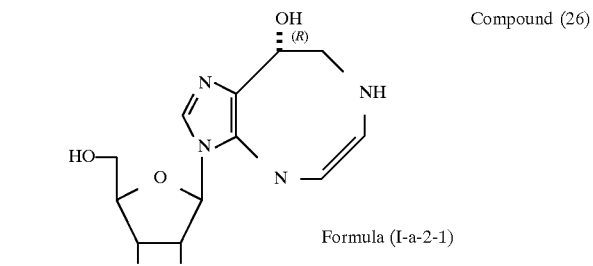

as a colorless solid (20 mg). $[\alpha]_D^{22}$+12° (c 0.1, water).

Also, 2'-deoxy-8-epi-2'-fluorocoformycin [compound (27)] having the following formula

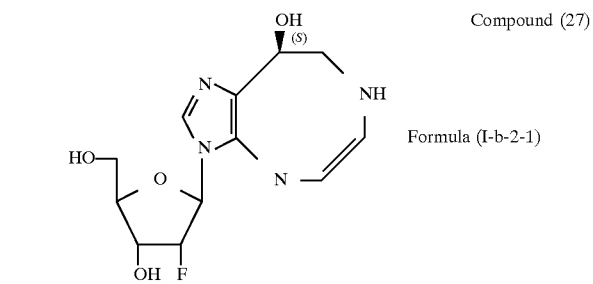

was obtained simultaneously as a colorless solid (17 mg).
$[\alpha]_D^{22}$–115° (c 0.09, water).

REFERENTIAL EXAMPLE 3

Preparation of 3,5-di-O-acetyl-2-chloro-2-deoxy-α,β-D-ribofuranosyl amine (1) Synthesis of 3,5-di-O-acetyl-2-chloro-2-deoxy-α,β-D-ribofuranosyl bromide [Compound (29)]

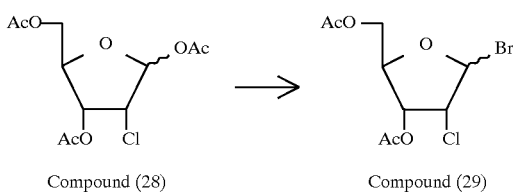

Compound (28)　　　　　Compound (29)

where Ac denotes acetyl group (the same abbreviation applies hereinafter).

3,5-Di-O-acetyl-2-chloro-2-deoxy-α,β-D-ribofuranosyl acetate [compound (28)] (the compound reported by J. P. Schaumberg et al., in "J. Org. Chem.", 50, pp. 1651–1656, 1985) (1.20 g) was dissolved in dichloromethane (25 ml). To the solution was added 30% hydrogen bromide in acetic acid (2.5 ml) and the resultant mixture was allowed to effect the reaction at room temperature overnight, so that the bromination of compound (28) took place. The reaction solution containing compound (29) thus produced was concentrated and then the acetic acid left therein was removed by azeotropic distillation with toluene. The titled compound (29) was thus obtained as a slightly yellowish syrup (1.32 g) Yield: 97%.

(2) Synthesis of 3,5-di-O-acetyl-2-chloro-2-deoxy-α,β-D-ribofuranosyl azide [Compound (30)]

Compound (29) obtained in step (1) above (1.05 g) was dissolved in acetonitrile (21 ml), to which were then added sodium azide (320 mg) and tetraethylammonium bromide (700 mg), and the resultant mixture was stirred at room temperature for 3 hours. The reaction solution so formed was concentrated to a small volume, then diluted with chloroform and the chloroform solution obtained was dried over anhydrous sodium sulfate and then concentrated to yield the titled compound (30) as a colorless syrup (887 mg). Yield: 96%.

Infrared absorption spectrum: 2110 cm$^{-1}$ ($N_3$)

(3) Synthesis of 3,5-di-O-acetyl-2-chloro-2-deoxy-α,β-D-ribofuranosyl amine [Compound (31)]

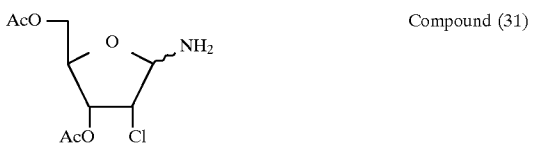

Compound (30) obtained in step (2) above (300 mg) was dissolved in dioxane (6 ml). The solution obtained was subjected to a catalytic reduction by blowing hydrogen therein at room temperature in the presence of palladium black as catalyst for 1 hour. The resulting reaction solution was filtered and the filtrate was concentrated to about a half volume and then diluted with dichloroethane (50 ml). The solution as diluted was dried over calcium chloride and concentrated to afford compound (31) as a colorless syrup (270 mg).

Rough yield: 99%.

EXAMPLE 3

Preparation of 2'-chloro-2'-deoxycoformycin and 2'-chloro-2'-deoxy-8-epicoformycin (1) Synthesis of tert-butyl 1-(3,5-di-O-acetyl-2-chloro-2-deoxy-α- and β-D-ribofuranosyl)-5-aminoimidazole-4-carboxylates [Compounds (33) and (32)]

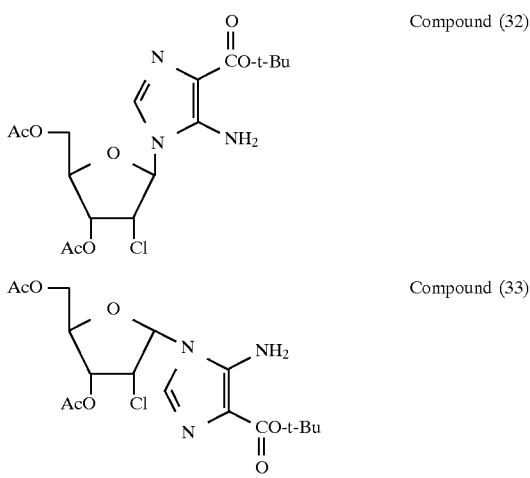

Compound (31) obtained in step (3) of Referential Example 3 (270 mg) was dissolved in dichloroethane (6 ml), to which was then added a solution of compound (6) as obtained in step (5) of Referential Example 1 (430 mg) in dichloroethane (9 ml). The resulting mixture was heated under reflux for 1 hour. There occurred the aminoimidazolation of compound (31), to produce compound (32) and compound (33) above.

The resulting reaction solution containing compounds (32) and (33) was concentrated and the resulting syrup was subjected to silica gel column chromatography (developer solvent: chloroform-ethyl acetate, 2:1) for the isolation and purification of the desired products, so that compound (33) was recovered as a colorless solid (80 mg) and compound (32) as a colorless solid (92 mg). The yields of compounds (33) and (32) as calculated from compound (30) were 18% and 20%, respectively.

(2) Synthesis of tert-butyl 1-(3,5-di-O-acetyl-2-chloro-2-deoxy-β-D-ribofuranosyl)-5-phthalimidoimidazole-4-carboxylate [Compounds (34)]

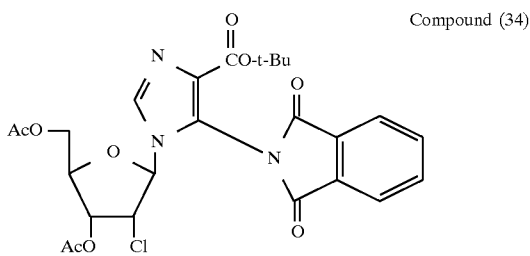

Compound (32) obtained in step (1) above (200 mg) was dissolved in N,N-dimethylformamide (3 ml), to which were then added potassium carbonate (73 mg) and N-carboethoxyphthalimide (117 mg). The resultant mixture was stirred at room temperature for 2 hours. The reaction solution so obtained was filtered and the filtrate was concentrated to leave a syrup. The syrup was purified by silica gel column chromatography (developer solvent:toluene-ethyl acetate, 1:1), to recover the titled compound (34) as a colorless solid (239 mg). Yield: 91%.

(3) Synthesis of 1-(3,5-di-O-acetyl-2-chloro-2-deoxy-β-D-ribofuranosyl)-5-phthalimidoimidazole-4-carboxylic acid [Compounds (35)]

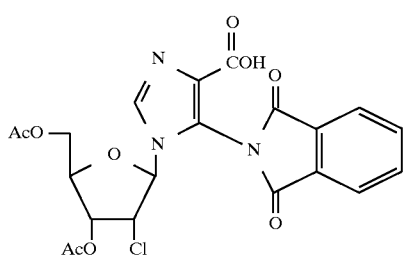

Compound (35)

Compound (34) obtained in step (2) above (1.50 g) was dissolved in a mixture of trifluoroacetic acid-dichloromethane (1:4) (25 ml), and the solution so obtained was allowed to stand at room temperature overnight so that there occurred de-esterification of compound (34). The resulting reaction solution was concentrated to leave a solid. This solid was then washed with diethyl ether to yield the titled compound (35) (1.31 g) which was insoluble in diethyl ether (1.31 g). Yield: 97%.

(4) Synthesis of 1-(3,5-di-O-acetyl-2-chloro-2-deoxy-β-D-ribofuranosyl)-4-chloroacetyl-5-phthalimidoimidazole [Compounds (38)]

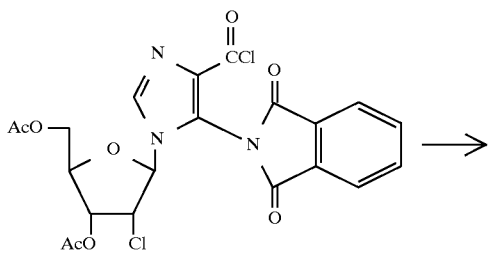

Compound (36)

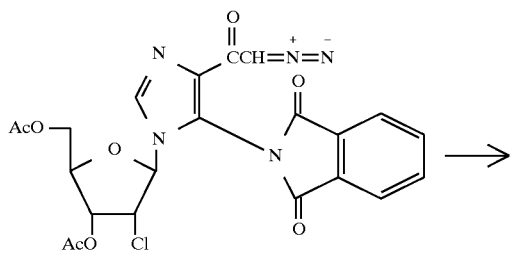

Compound (37)

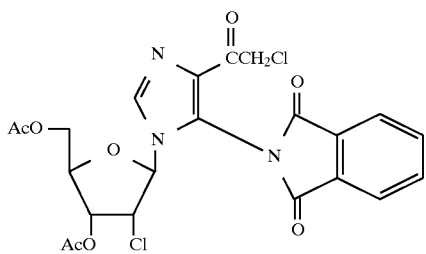

Compound (38)

Compound (35) obtained in step (3) above (180 mg) was dissolved in tetrahydrofuran (2 ml), to which was then added under ice-cooling N,N-dimethylchloroforminium chloride (93 mg), and the resultant mixture was stirred at that temperature for 0.5 hours to conduct the reaction intended.

There occurred the chlorination reaction of compound (35) to give the chloroformyl compound (36) shown above. Then, the resulting reaction solution containing compound (36) was added to a 0.2M diazomethane-diethyl ether solution (25 ml), and the mixture so obtained was allowed to effect the reaction at room temperature for 0.5 hours. Thus, there occurred the diazomethylation reaction to produce the diazo compound (37) above shown.

The resulting reaction solution containing compound (37) was concentrated to leave a solid comprising compound (37). The resulting solid was dissolved in dichloromethane (5 ml), to which was added a solution of 1M hydrogen chloride in diethyl ether (0.5 ml). The mixture obtained was allowed to effect the reaction for 0.5 hours. The reaction solution so formed was diluted with dichloromethane and then washed with water. The organic layer so separated was dried over anhydrous sodium sulfate and concentrated, to afford the titled compound (38) (170 mg). Yield as calculated from compound (35): 89%.

(5) Synthesis of 1-(3,5-di-O-acetyl-2-chloro-2-deoxy-β-D-ribofuranosyl)-5-amino-4-chloroacetylimidazole [Compound (39)]

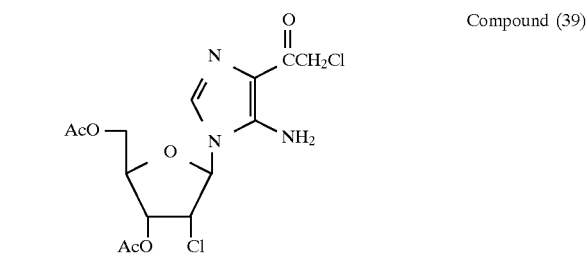

Compound (39)

Compound (38) obtained in step (4) above (310 mg) was dissolved in dichloromethane (12 ml), to which was then added hydrazine monohydrate (0.032 ml) under cooling at 0° C. The resultant mixture was stirred at that temperature for 1 hour to conduct the reaction intended and thereby afford the titled compound (39). The resulting reaction solution containing compound (39) was filtered and the filtrate was concentrated to leave a solid, which was purified by silica gel column chromatography (developer solvent: toluene-ethyl acetate, 1:2), to yield the titled compound (39) as a colorless solid (221 mg). Yield: 95%.

(6) Synthesis of 1-(3,5-di-O-acetyl-2-chloro-2-deoxy-β-D-ribofuranosyl)-5-amino-4-azidoacetylimidazole [Compound (40)]

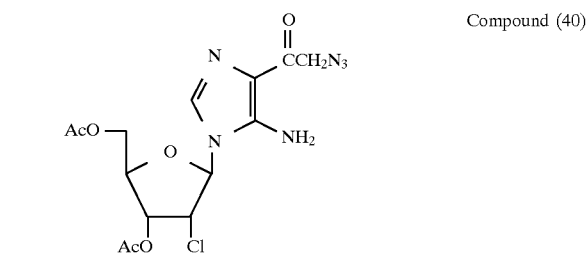

Compound (40)

Compound (39) obtained in step (5) above (170 mg) was dissolved in N,N-dimethylformamide (3.4 ml), to which was added sodium azide (45 mg). The resultant mixture was stirred at room temperature for 1 hour to conduct the reaction intended. The reaction solution obtained was concentrated and the residue was extracted with ethyl acetate. The extract was washed with water, dried over anhydrous sodium sulfate and concentrated to leave a yellow syrup. The syrup was purified by silica gel column chromatography (developer solvent: toluene-ethyl acetate, 1:2) to afford the titled compound (40) as a colorless solid (159 mg). Yield: 92%.

(7) Synthesis of 1-(3,5-di-O-acetyl-2-chloro-2-deoxy-β-D-ribofuranosyl)-5-amino-4-aminoacetylimidazole

[Compound (41)]

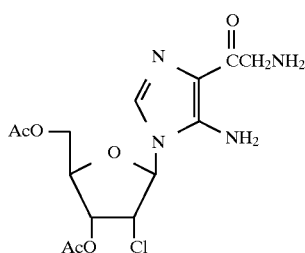

Compound (40) obtained in step (6) above (100 mg) was dissolved in methanol (4 ml), to which was then added a solution of 1M hydrogen chloride in methanol (0.37 ml). The resulting solution was subjected to a catalytic reduction by blowing hydrogen therein at room temperature in the presence of palladium black as catalyst for 1 hour. The reaction solution so obtained was filtered and the filtrate was concentrated to leave a solid which was then washed with diethyl ether. Thus, the titled compound (41) was recovered as a solid (102.5 mg) which was insoluble in diethyl ether.

(8) Synthesis of 3-(3,5-di-O-acetyl-2-chloro-2-deoxy-β-D-ribofuranosyl)-6,7-dihydroimidazo[4,5-d][1,3]diazepin-8 (3H)-one [Compound (43)]

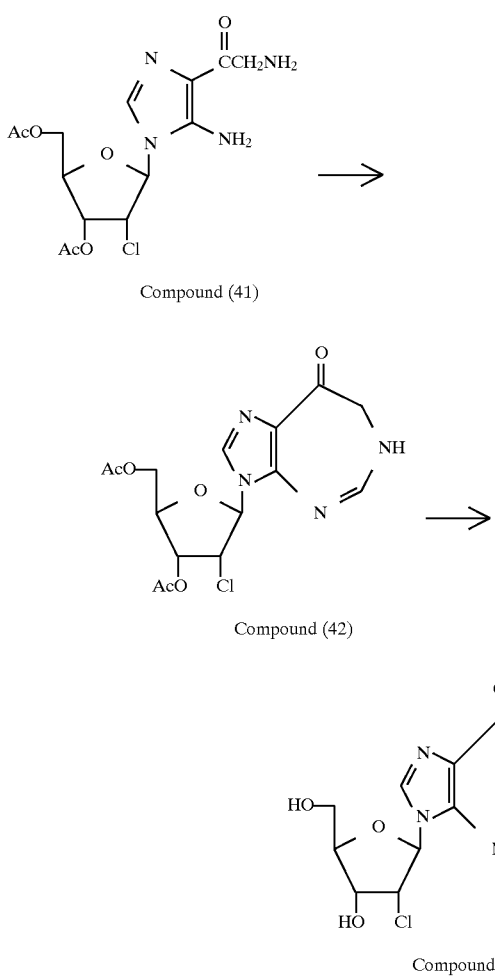

Compound (41) obtained in step (7) above (102.5 mg) was dissolved in N,N-dimethylformamide (2 ml), to which was then added triethyl orthoformate (0.62 ml). The resultant mixture was allowed to effect the reaction at room temperature overnight and thus form the 1,3-diazepinone ring, giving compound (42). The reaction solution so obtained was neutralized by adding a small amount of triethylamine and then concentrated to yield a yellow solid comprising compound (42) (140 mg).

The above solid containing compound (42) was dissolved in methanol (4 ml), to which was added a solution of 0.5M sodium methylate in methanol (1 ml). The mixture so obtained was allowed to effect the reaction at room temperature for 1 hour (for de-acetylation) and to give compound (43). The resulting reaction solution containing compound (43) was neutralized by adding thereto an ion exchange resin, Amberlite CG-120 (H$^+$-cycle) (100–200 mesh) and then filtered. The filtrate was concentrated and the resulting syrup was purified by silica gel column chromatography (developer solvent:chloroform-methanol, 3:1), thus to afford the titled compound (43) as a colorless solid (53 mg). Yield as calculated from compound (40): 71%.

(9) Synthesis of 2'-chloro-2'-deoxycoformycin (2'-chloropentostatin) [Compound (44)] and 2'-chloro-2'-deoxy-8-epicoformycin [Compound (45)]

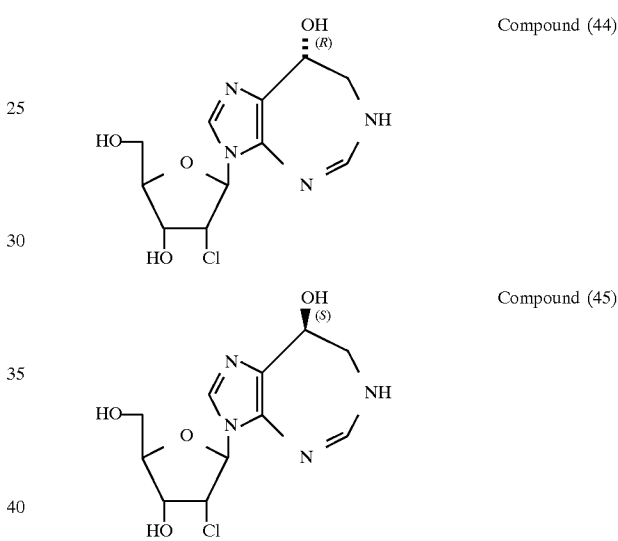

Compound (43) obtained in step (8) above (28 mg) was dissolved in a mixture of methanol-water (1:1) (1.2 ml), to which was then added lithium borohydride (1.0 mg) (or sodium borohydride, 1.8 mg). The resultant mixture was allowed to effect the reaction at room temperature for 1 hour, so that the reduction of the 8-oxo group of compound (43) into hydroxyl group occurred.

An amount of dry ice was added to the resulting reaction solution to decompose the excess reagents and the resulting solution was subjected, as a whole, to preparative high pressure liquid chromatography with using a reversed phase column (Senshu Pak. ODS-H-5251) (mobile phase: methanol-water, 1:9) for the isolation and purification. There were thus obtained both of the titled compound (44) as colorless crystals (12.7 mg; yield: 45%) and the titled compound (45) as a colorless solid (12.1 mg; yield: 43%).

It is added that compound (44) corresponded to some known compounds, i.e., 2'-chloropentostatin as reported by J. P. Schaumberg et al., in "J. Org. Chem.", 50, pp. 1651–1656 (1985); and also to adechlorin as reported by S. Omura et al., in The Journal of Antibiotics, 38, pp. 1008–1015 (1985).

REFERENTIAL EXAMPLE 4

Preparation of 3,5-di-O-acetyl-2-chloro-2-deoxy-α,β-D-arabinofuranosyl amine (1) Synthesis of 3,5-di-O-acetyl-2-chloro-2-deoxy-α,β-D-arabinofuranosyl azide [Compound (47)]

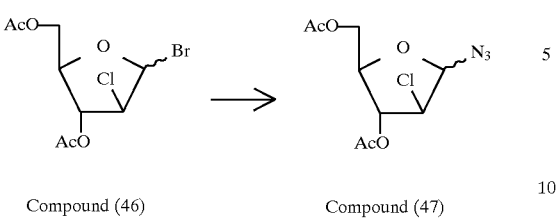

Compound (46)      Compound (47)

3,5-di-O-acetyl-2-chloro-2-deoxy-α,β-D-arabinofuranosyl bromide [compound (46)] (see K. A. Watanabe et al., "J. Med. Chem.", 26, pp. 152–156, 1983) (350 mg) was dissolved in acetonitrile (7 ml), to which were then added sodium azide (108 mg) and tetraethylammonium bromide (230 mg). The resultant mixture was stirred at room temperature for 2 hours to effect the reaction intended and thus produce compound (47).

The resulting reaction solution containing the compound (47) was concentrated to a small volume and then diluted with chloroform. The chloroform solution so obtained was washed with water, dried over anhydrous sodium sulfate and concentrated to afford the titled compound (47) as a colorless syrup (293 mg). Yield: 95%.

Infrared absorption spectrum: 2110 cm$^{-1}$ (N$_3$)

(2) Synthesis of 3,5-di-O-acetyl-2-chloro-2-deoxy-α,β-D-arabinofuranosyl amine [Compound (48)]

Compound (47) obtained in step (1) above (70 mg) was dissolved in dioxane (2 ml). The solution obtained was subjected to a catalytic reduction by blowing hydrogen therein at room temperature for 1 hour in the presence of palladium black as catalyst, so that the azido group of compound (47) was converted into amino group. The resulting reaction solution was filtered and the filtrate was concentrated to about a half volume and the concentrate was diluted with dichloroethane (20 ml). The solution so obtained was dried over calcium chloride, after which a small amount of triethylamine was added. The resulting mixture was concentrated to leave the titled compound (48) as a colorless syrup (62 mg). Rough yield: 98%.

EXAMPLE 4

Preparation of 2'-chloro-2'-deoxy-2'-epicoformycin and 2'-chloro-2'-deoxy-8,2'-diepicoformycin 3,5-Di-o-acetyl-2-chloro-2-deoxy-α,β-D-arabinofuranosyl amine [compound (48)] as obtained in Referential Example 4 as a colorless syrup (62 mg) was dissolved in dichloroethane (1.5 ml). To the resulting solution was added a solution in dichloroethane (2 ml) of compound (6) [the compound of formula (M)] prepared in Referential Example 1 (100 mg). The resulting mixture was heated under reflux for 1 hour to conduct the reaction intended.

There were thus produced tert-butyl 1-(3,5-di-O-acetyl-2-chloro-2-deoxy-β-D-arabinofuranosyl)-5-aminoimidazole-4-carboxylate [compound (49)] and the α-isomer thereof [compound (50)] in the reaction solution as formed. The reaction solution was subjected to chromatography in the same manner as in step (1) of Example 1, to give compound (49) (21.6 mg).

Compound (49) was used for the series of the subsequent steps for the intended synthesis, in accordance with the procedures of steps (2) to (12) of Example 1. Thus, there was obtained 2'-chloro-2'-deoxy-2'-epicoformycin [compound (51)] having the following formula

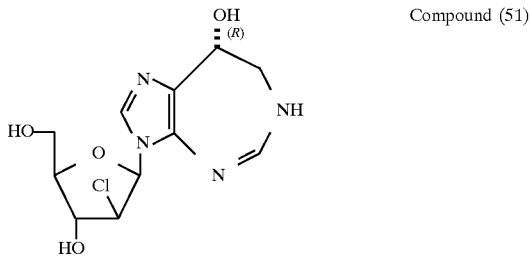

as a colorless solid (3.1 g).

Infrared absorption spectrum (KBr disk): 3350, 1630, 1100 cm$^{-1}$.

Also, 2'-chloro-2'-deoxy-8,2'-diepicoformycin [compound (52)] having the following formula

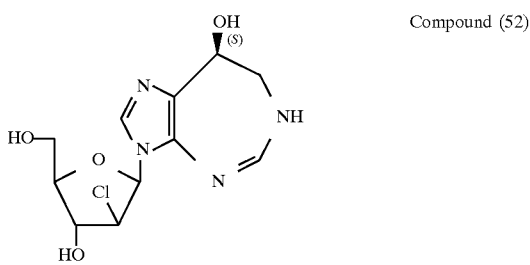

was obtained as a colorless solid (2.9 mg).

What we claim is:

1. A process for the preparation of a 2'-deoxy-2'-halocoformycin and a 2'-deoxy-8-epi-2'-halocoformycin or stereoisomers thereof, which comprises the following eleven numbered steps:

(1) contacting tert-butyl 1-(3,5-di-O-acyl-2-deoxy-2-halo-β-D-ribofuranosyl or arabinofuranosyl)-5-aminoimidazole-4-carboxylate (II)

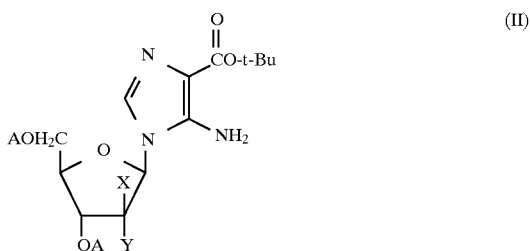

wherein A represents a hydroxyl-protecting acyl group selected from the group consisting of lower alkanoyl groups and a benzoyl group, either one of X and Y is a hydrogen and the other is a halogen, and t-Bu is a tertiary butyl group, with N-carboalkoxyphthalimide (III)

wherein R is a lower alkyl group, or with phthalic anhydride, to make tert-butyl 1-(3,5-di-O-acyl-2-deoxy-2-halo-β-D-ribofuranosyl or arabinofuranosyl)-5-(N-phthalimido) imidazole-4-carboxylate (IV)

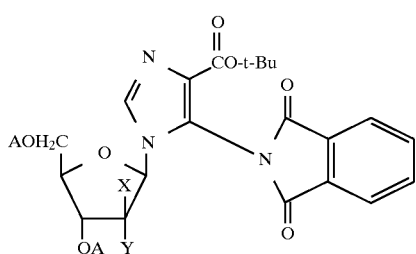

(IV)

wherein A, X, Y and t-Bu have the same meanings as defined above;

(2) contacting intermediate (IV) with trifluoroacetic acid to remove the tertiary butyl group, thereby making 1-(3,5-di-O-acyl-2-deoxy-2-halo-β-D-ribofuranosyl or arabinofuranosyl)-5-(N-phthalimido)imidazole-4-carboxylic acid (V)

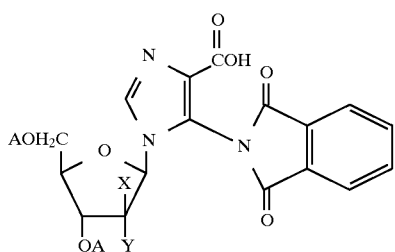

(V)

wherein A, X and Y have the same meanings as defined above;

(3) contacting the 4-carboxyl group of intermediate (V) with a chlorinating agent to produce a chloroformyl group, thereby making 1-(3,5-di-O-acyl-2-deoxy-2-halo-β-D-ribofuranosyl or arabinofuranosyl)-4-chloroformyl-5-(N-phthalimido)imidazole (VI)

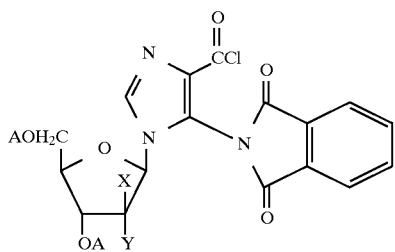

(VI)

wherein A, X and Y have the same meanings as defined above;

(4) contacting intermediate (VI) with diazomethane to make 1-(3,5-di-O-acyl-2-deoxy-2-halo-β-D-ribofuranosyl or arabinofuranosyl)-4-diazoacetyl-5-(N-phthalimido)imidazole (VII)

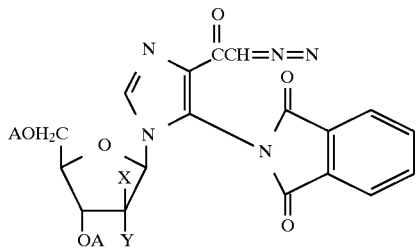

(VII)

wherein A, X and Y have the same meanings as defined above;

(5) contacting intermediate (VII) with hydrogen chloride in an organic solvent to make 1-(3,5-di-O-acyl-2-deoxy-2-halo-β-D-ribofuranosyl or arabinofuranosyl)-4-chloroacetyl-5-(N-phthalimido)imidazole (VIII)

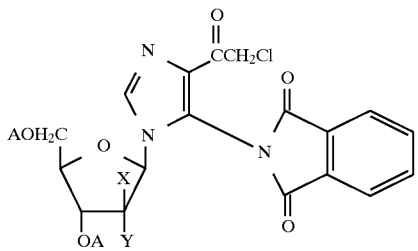

(VIII)

wherein A, X and Y have the same meanings as defined above;

(6) contacting intermediate (VIII) with hydrazine to cleave the phthalyl residue from the 5-phthalimido group, thereby making 1-(3,5-di-O-acyl-2-deoxy-2-halo-β-D-ribofuranosyl or arabinofuranosyl)-4-chloroacetyl-5-aminoimidazole (IX)

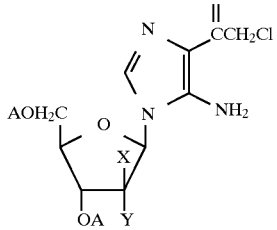

(IX)

wherein A, X and Y have the same meanings as defined above;

(7) contacting intermediate (IX) with an alkali metal azide to make 1-(3,5-di-O-acyl-2-deoxy-2-halo-β-D-ribofuranosyl or arabinofuranosyl)-5-amino-4-azidoacetylimidazole (X)

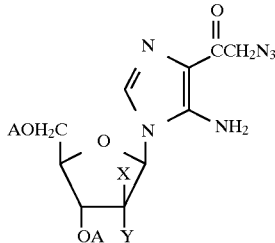

(X)

wherein A, X and Y have the same meanings as defined above;

(8) catalytically reducing the 4-azidoacetyl group of intermediate (X) with hydrogen to produce an aminoacetyl substituent, thereby making 1-(3,5-di-O-acyl-2-deoxy-2-halo-β-D-ribofuranosyl or arabinofuranosyl)-5-amino-4-aminoacetylimidazole (XI)

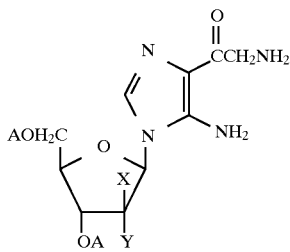

(XI)

wherein A, X and Y have the same meanings as defined above;

(9) contacting intermediate (XI) with triethyl orthoformate (XII)

(XII)

to make 3-(3,5-di-O-acyl-2-deoxy-2-halo-β-D-ribofuranosyl or arabinofuranosyl)-6,7-dihydroimidazolo[4,5-d]-[1,3]-diazepin-8(3H)-one (XIII)

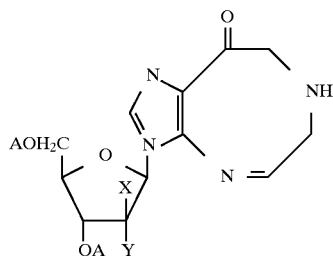
(XIII)

wherein A, X and Y have the same meanings as defined above;

(10) contacting intermediate (XIII) with a reagent effective for the removal of hydroxyl protecting groups (A) to make 3-(3,5-di-O-acyl-2-deoxy-2-halo-β-D-ribofuranosyl or arabinofuranosyl)-6,7-dihydroimidazolo[4,5-d]-[1,3]-diazepin-8(3H)-one (XIII-a)

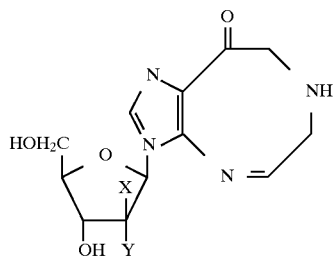
(XIII-a)

wherein X and Y have the same meanings as defined above; and

(11) reducing intermediate (XIII-a) with lithium or sodium borohydride to make a mixture of compounds (I-a)

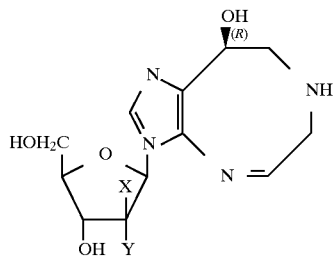
(I-a)

known individually as 2'-halo-2'-deoxycoformycin {(I-a) where X is hydrogen and Y is halogen} and 2'-deoxy-2'-epi-2'-halocoformycin {(I-a) where X is halogen and Y is hydrogen}; or (I-b)

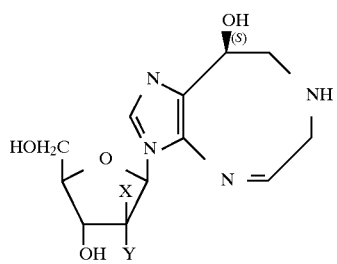
(I-b)

known individually as 2'-halo-8-epi-2'-deoxycoformycin {(I-b) where X is hydrogen and Y is halogen} and 2'-deoxy-8,2'-diepi-2'-halocoformycin {(I-b) where X is halogen and Y is hydrogen}.

2. A process according to claim 1, where a tert-butyl 1-(3,5-di-O-acyl-2-deoxy-2-halo-β-D-arabinofuranosyl)-5-aminoimidazole-4-carboxylate (II) is used as a starting compound, thereby to afford a 2'-deoxy-2'-epi-2'-halocoformycin of the following formula (I-a-1)

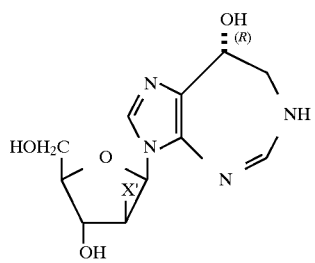
(I-a-1)

wherein X' represents a halogen atom chosen from fluorine, chlorine, bromine and iodine, and a 2'-deoxy-8,2'-diepi-2'-halocoformycin of the following formula (I-b-1)

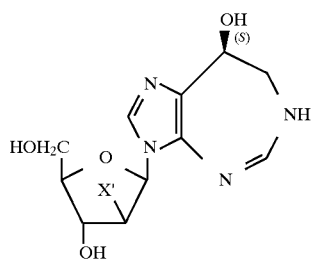
(I-b-1)

wherein X' is as defined above.

3. A process according to claim 1, where a tert-butyl 1-(3,5-di-O-acyl-2-deoxy-2-halo-β-D-ribofuranosyl)-5-aminoimidazole-4-carboxylate (II) is used as a starting compound, thereby to afford a 2'-deoxy-2'-halocoformycin of the following formula (I-a-2)

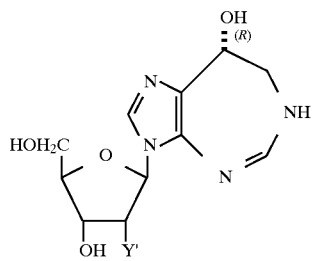
(I-a-2)

wherein Y' represents a halogen atom chosen fluorine, chlorine, bromine and iodine, and a 2'-deoxy-8-epi-2'-halocoformycin of the following formula (I-b-2)

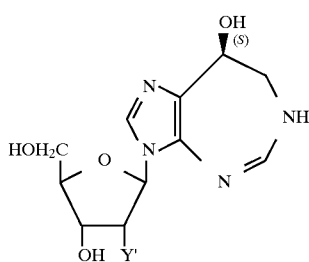

(I-b-2)

wherein Y' is as defined above.

4. A tert-butyl 1-(3,5-di-O-acetyl or benzoyl-2-deoxy-2-halo-β-D-ribofuranosyl or arabinofuranosyl)-5-aminoimidazole-4-carboxylate represented by the following formula (II-a)

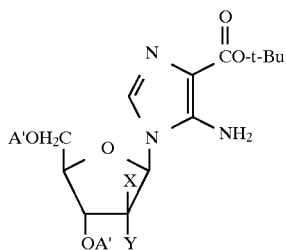

(II-a)

wherein either one of X and Y is a hydrogen atom and the other is a halogen atom, A' is acetyl group or benzoyl group, and t-Bu is tertiary-butyl group.

5. A tert-butyl 1-(3,5-di-O-acetyl or benzoyl-2-deoxy-2-halo-β-D-ribofuranosyl or arabinofuranosyl)-5-phthalimidoimidazole-4-carboxylate represented by the following formula (IV-a)

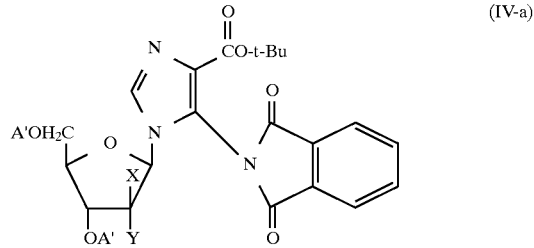

(IV-a)

wherein either one of X and Y is a hydrogen atom and the other is a halogen atom, A' is acetyl group or benzoyl group, and t-Bu is tertiary-butyl group.

* * * * *